US007687511B2

(12) United States Patent
Pullela et al.

(10) Patent No.: US 7,687,511 B2
(45) Date of Patent: Mar. 30, 2010

(54) SUBSTITUTED DIHYDROPYRIMIDINES, DIHYDROPYRIMIDONES AND DIHYDROPYRIMIDINETHIONES AS CALCIUM CHANNEL BLOCKERS

(76) Inventors: Phani Kumar Pullela, 3055 N. Oakland Ave., Apt. #310, Milwaukee, WI (US) 53211; Paramashivappa Rangappa, 26-1797 Main St. W., Hamilton, Ontario (CA) L8S 1H6; Srinivasa Rao Alapati, Apt. 303, 15 Manito Shelters, Dinnur Main Rd., R.T. Nagar, Bagalore (IN) 560032; Pillarisetti V. Subbarao, 41/3 Aarathi Apartments, 13 Cross Rd., Malleswaram, Bangalore (IN) 560003

( * ) Notice: Subject to any disclaimer, the term of this patent is extended or adjusted under 35 U.S.C. 154(b) by 134 days.

(21) Appl. No.: 11/938,699

(22) Filed: Nov. 12, 2007

(65) Prior Publication Data

US 2008/0125449 A1 May 29, 2008

Related U.S. Application Data

(63) Continuation of application No. 10/459,120, filed on Jun. 10, 2003, now abandoned.

(60) Provisional application No. 60/389,984, filed on Jun. 17, 2002.

(51) Int. Cl.
*C07D 239/22* (2006.01)
*A61K 31/505* (2006.01)

(52) U.S. Cl. ...................................... 514/274; 544/318

(58) Field of Classification Search ................. 544/318; 514/274

See application file for complete search history.

(56) References Cited

U.S. PATENT DOCUMENTS

| | | | |
|---|---|---|---|
| 4,675,321 | A | 6/1987 | Baldwin et al. |
| 5,202,330 | A | 4/1993 | Atwal et al. |

FOREIGN PATENT DOCUMENTS

| | | |
|---|---|---|
| EP | 1 193 259 A1 | 4/2002 |
| WO | WO 97/21687 | 6/1997 |

OTHER PUBLICATIONS

Putney et al., *Mechanisms of capacitative calcium entry*, Journal of Cell Science, vol. 114 (12), pp. 2223-2229, (2001).

*Primary Examiner*—Deepak Rao
(74) *Attorney, Agent, or Firm*—Knobbe, Martens, Olson & Bear, LLP

(57) ABSTRACT

The present invention is directed in part towards methods of modulating the function of calcium channels with pyrimidine-based compounds. In addition, the invention describes methods of preventing and treating calcium channel-related abnormal conditions in organisms with a compound identified by the invention. Furthermore, the invention pertains to pyrimidine-based compounds and pharmaceutical compositions comprising these compounds.

27 Claims, No Drawings

SUBSTITUTED DIHYDROPYRIMIDINES, DIHYDROPYRIMIDONES AND DIHYDROPYRIMIDINETHIONES AS CALCIUM CHANNEL BLOCKERS

RELATED APPLICATIONS

The present application is a continuation of U.S. patent application Ser. No. 10/459,120, filed Jun. 10, 2003, which claims priority to U.S. Provisional Application Ser. No. 60/389,984, filed Jun. 17, 2002. The entire disclosure of these applications, including any drawings, is hereby incorporated by reference.

BACKGROUND OF THE INVENTION

1. Field of the Invention

The present invention relates to certain dihydropyrimidine, dihydropyrimidone and dihydropyrimidinethione compounds that can modulate the activity of calcium channels. These compounds can also be used for the treatment of diseases, such as cardiovascular disease, that are associated with calcium channels.

2. Description of the Related Art

The pharmacological function and importance of calcium antagonists or calcium channel blockers, has been well documented. See, for example, R. A. Janis and D. J. Triggle "*New developments in $Ca^{2+}$ channel antagonists*" *Journal of Medicinal Chemistry,* 26, 775-785 (1983). Among the calcium antagonists, 4-aryl-1,4-dihydropyridine-3,5-dicarboxylic diesters (DUPs) of the nifedipine type have become almost indispensable for the treatment of cardiovascular diseases. For a review on Structure Activity Relations (SAR) see, S. Goldmann and J. Stoltefuss "1,4-*Dihydropyridine: Effects of chirality and conformation on the calcium antagonist and calcium agonist activities*" *Angewandte Chemie International Edition* (*English*) 30, 1559-1578 (1991). It was well documented that substitution on 4-phenyl ring is very crucial for pharmacological activity. Substituents at ortho or meta position improve the activity, whereas para substitution invariably decrease the activity. It was also published that bulkiness of ortho substituent, improves the calcium antagonist activity. B. Loev, M. M. Goodman, K. M. Snader, R. Tedeschi, E. Macko, "*Hantzsch-Type Dihydropyridine hypotensive Agents*", *Journal of Medicinal Chemistry* 17, 956-965 (1974). Though dihydropyridines of nifedipine type have been used as anti-hypertensive agents, they have a serious disadvantage in treatment of hypertension. Since their plasma half-lives are relatively short, these drugs must be administered repeatedly to achieve enough clinical efficacy (Buhler, F. R.; Hukhten, U. L.; Kiowski, W. J. *Cardiovasc. Pharamcol.* 1982, 4, 350. Belz, G. G.; Spies, G. *Excerpta Med.* 1986, 177). This made researchers to look for more structural variations in the dihydropyridines ring. A number of compounds were known with variation in the dihydropyridine ring like dihydropyran (Bayer A. G. patent, DE 2235406.9, 1972), dihydrothiopyran (Bayer A. G. patent, DE 3212737.5, 1982), dihydropyridazine (Bayer A. G. patent, DE 834624, 1978), dihydropyrazine (Bayer A. G. patent, DE 3400765, 1984) and dihydropyrimidines (Baldwin et al, U.S. Pat. No. 4,675,321, 1987). Among these, dihydropyrimidines was the most potent class, which offered both potency and longer bioavailability.

Voltage-gated calcium channels are large trans-membrane proteins that regulate the intracellular concentration of calcium ions. They are classified into high (HVA) and low (LVA) voltage-activated channels, according to the membrane potential at which they are activated (E. Carbone and H. D. Lux. "*A low voltage activated, fully inactivating Ca channel in vertebrate sensory neurons*" *Nature,* 310, 501-502, 1984; B. Nilius, P. Hess, J. B. Lansman and R. W. Tsien "*A novel type of cardiac calcium channel in ventricular cells.*" *Nature,* 316, 443-446, 1985; M. C. Nowycky, A. P. Fox, R. W. Tsien. "*Three types of neuronal calcium channels with different calcium agonist sensitivity*" *Nature* 316, 440-443, 1985). LVA channels open and inactivate very fast, but deactivate about 10-100 times slower than HVA calcium channels. HVA channels require stronger membrane depolarizations to activate and can be divided further into N. P/Q,R and L-types based on their pharmacological properties. LVA channels can be detected in various tissues such as heart, brain, dorsal root ganglia and adrenal gland. The use of different search algorithms on mammalian expressed sequence tagged cDNAs or on similar sequences of the nematode *Caenorhabditis elegans* led to the identification of several genes, three of which encoded LVA calcium channels (T-type channels) and they have been named as $\alpha_{1G}$, $\alpha_{1H}$, $\alpha_{1I}$; (For Review, L. Lacinova, N. Klugbauer, F. Hofmann "*Low voltage activated calcium channels: from genes to function*" *Gen. Physiol. Biophys,* 19, 121-136, 2000. Of the above stated types of calcium channels, L-type channels received wide attention. Among the L-type channel blockers, Dihydropyridines (DHPs), dihydropyrimidines and dihydropyrimidinones are the most widely studied. But, most of the DHPs, dihydropyrimidines and dihydropyrimidinones are not selective against T-type channels and compounds inhibiting the T-type channels from these classes of compounds are still sparse.

SUMMARY OF THE INVENTION

Disclosed are compounds of Formula I (I)

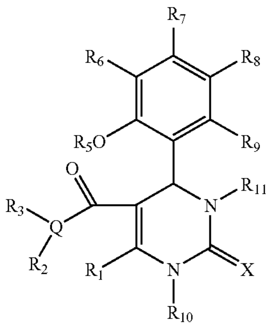

or a pharmaceutically acceptable salt, amide, ester, or prodrug thereof, where a) $R_1$-$R_3$ and $R_5$-$R_8$, are each independently selected from the group consisting of hydrogen, halogen, perhaloalkyl, nitro, amino, a diazo salt, optionally substituted lower alkyl, alkoxy, optionally substituted lower alkylene and optionally substituted five-membered or optionally substituted six-membered heteroaryl ring or optionally substituted six-membered aryl or heteroaryl ring, wherein the lower alkyl and the lower alkylene moieties are each independently and optionally substituted with one or more substituents selected from the group consisting of halogen, perhaloalkyl, nitro, amino, hydroxy, alkoxy, sulfhydryl, thioether, cyano, amido, ester, and

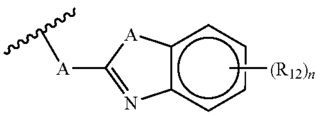

A is selected from the group consisting of oxygen, sulfur, sulfoxide, sulfone, and —NH;

$R_{12}$ is selected from the group consisting of hydrogen, hydroxy, alkoxy, haloalkoxy, halogen, haloalkyl, perhaloalkyl, nitro, amino, and a diazo salt;

n is between 0-4; and said ring moieties are each independently and optionally substituted with one or more substituents selected from the group consisting of lower alkyl, lower alkylene, b) $R_9$ is selected from the group consisting of hydrogen, alkyl, alkylene, and a five-membered or six-membered heteroaryl ring or a six-membered aryl or heteroaryl ring, optionally substituted with one or more substituents selected from the group consisting of lower alkyl, lower alkylene, halogen, perhaloalkyl, nitro, amino, cyano, amido, and ester; and c) $R_{10}$ is selected from the group consisting of hydrogen and lower alkyl d) $R_{11}$ is selected from the group consisting of:

i) hydrogen, alkyl, alkoxy, alkylene, and a five-membered or six-membered heteroaryl ring or a six-membered aryl or heteroaryl ring, optionally substituted with one or more substituents selected from the group consisting of lower alkyl, lower alkylene, halogen, perhaloalkyl, nitro, amino, cyano, amido, and ester;

ii) COY wherein Y is $C_1$-$C_8$ alkyl, $C_1$-$C_8$ alkoxy or $NR_{13}R_{14}$, wherein $R_{13}$ is hydrogen or $C_1$-$C_8$ alkyl and $R_{14}$ is hydrogen, $C_1$-$C_8$ alkyl, or $C_1$-$C_{14}$ phenalkyl;

iii) X or COX wherein X is

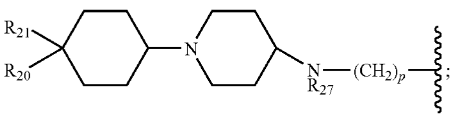

;

iv) halogen, $CF_3$, cyano, nitro, $COONHR_{25}$, $COON(R_{25})_2$, $COOSO_2R_{28}$, $COONR_{25}SO_2N(R_{25})_2$, $CO_2R_{25}$, $COON(R_{25})_2$, $COOSO_2N(R_{25})_2$, $COOSO_2R_{28}$.

v) $CONR_{15}R_{16}$, wherein $R_{15}$ is selected from the group consisting of hydrogen, alkyl cycloalkyl, aryl, or arylalkyl and $R_{16}$ is selected from the group consisting of hydrogen, alkyl cycloalkyl, aryl, or halosubstituted alkyl or $R_{15}$ and $R_{16}$ taken together with the nitrogen atom to which they are attached form 1-pyrrolidinyl, 1-piperidinyl, 1-azepinyl, 4-morpholinyl, 4-thiamorpholinyl, 1-piperazinyl, 4-diarylalkyl-1-piperazinyl, each of which is optionally substituted with one or more substituents selected from the group consisting of alkyl alkoxy, alkylthio, halo, trifloromethyl, or hydroxy;

vi) Z, COOZ, or C(O)(NH)Z, wherein Z is selected from the group consisting of

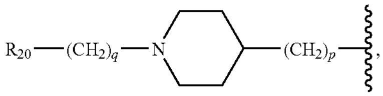

,

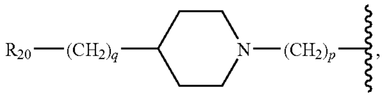

,

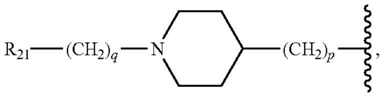

, and

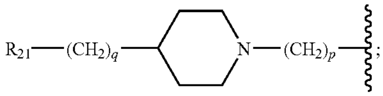

;

wherein

A) p and q are each independently 0-10;

B) $R_{20}$ is phenyl optionally substituted with one or more substituents independently selected from the group consisting of halogen, $CF_3$, cyano, nitro, $N(R_{25})_2$, $NR_{25}CONR_{27}$, $NR_{25}CON(R_{27})_2$, $NR_{25}SO_2R_{28}$, $NR_{25}SO_2N(R_{27})_2$, $(CH_2)_{0-4}CO_2R_{25}$, $(CH_2)_{0-4}CON(R_{25})_2$, $(CH_2)_{0-4}SO_2N(R_{25})_2$, $(CH_2)_{0-4}SO_2R_{28}$, and $C_{1-4}$ alkyl;

C) $R_{21}$ is selected from the group consisting of hydrogen, cyano, $OR_{28}$, $COOR_{25}$, $CON(R_{25})_2$, and phenyl optionally substituted with one or more substituents independently selected from the group consisting of halogen, $CF_3$, cyano, nitro, $N(R_{25})_2$, $NR_{25}CONR_{27}$, $NR_{25}CON(R_{27})_2$, $NR_{25}SO_2R_{28}$, $NR_{25}SO_2N(R_{27})_2$, $(CH_2)_{0-4}CO_2R_{25}$, $(CH_2)_{0-4}CON(R_{25})_2$, $(CH_2)_{0-4}SO_2N(R_{25})_2$, $(CH_2)_{0-4}SO_2R_{28}$, and $C_{1-4}$ alkyl;

D) $R_{25}$ and $R_{27}$ are each independently selected from hydrogen, $C_{1-8}$ alkyl, $C_{3-8}$ cycloalkyl, $(CH_2)_{0-4}CF_3$; and E) $R_{28}$ is selected from the group consisting of hydrogen, $C_{1-8}$ alkyl, $C_{3-8}$ cycloalkyl, and $(CH_2)_{0-4}CF_3$;

e) X is oxygen or sulfur; and f) Q is oxygen or nitrogen; provided that when Q is oxygen $R_3$ does not exist.

Also disclosed are pharmaceutical compositions comprising a compound of Formula I, and a physiologically acceptable carrier, diluent, or excipient, or a combination thereof.

In addition, a method of modulating the activity of a calcium channel in a cell comprising the step of contacting the cell with a compound of Formula I is disclosed.

Furthermore, disclosed is a method of treating a disease associated with a cellular calcium channel comprising:

a) identifying a subject in need of such treatment;

b) administering to the subject a therapeutically effective amount of a compound of Formula I.

DETAILED DESCRIPTION OF THE PREFERRED EMBODIMENTS

Here, we report a novel series of di- and tetrahydropyrimidine. These compounds will exhibit activity as calcium channel antagonists, and can be used for the various purposes for which these types of compounds are known.

I. Compounds of the Invention

Thus, an aspect of the present invention relates to a compound of Formula I (I)

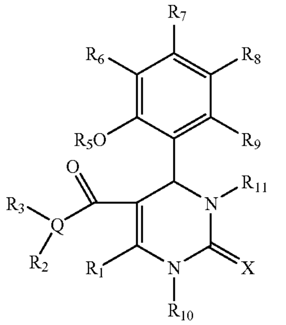

or a pharmaceutically acceptable salt, amide, ester, or prodrug thereof, wherein a) $R_1$-$R_3$ and $R_5$-$R_8$, are each independently selected from the group consisting of hydrogen, halogen, perhaloalkyl, nitro, amino, a diazo salt, optionally substituted lower alkyl, alkoxy, optionally substituted lower alkylene and optionally substituted five-membered or optionally substituted six-membered heteroaryl ring or optionally substituted six-membered aryl or heteroaryl ring, wherein said lower alkyl and said lower alkylene moieties are each independently and optionally substituted with one or more substituents selected from the group consisting of halogen, perhaloalkyl, nitro, amino, hydroxy, alkoxy, sulfhydryl, thioether, cyano, amido, ester, and

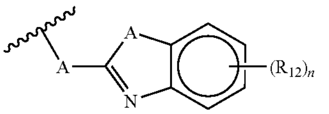

A is selected from the group consisting of oxygen, sulfur, sulfoxide, sulfone, and —NH;

$R_{12}$ is selected from the group consisting of hydrogen, hydroxy, alkoxy, haloalkoxy, halogen, haloalkyl, perhaloalkyl, nitro, amino, and a diazo salt;

n is between 0-4; and said ring moieties are each independently and optionally substituted with one or more substituents selected from the group consisting of lower alkyl, lower alkylene, b) $R_9$ is selected from the group consisting of hydrogen, alkyl, alkylene, and a five-membered or six-membered heteroaryl ring or a six-membered aryl or heteroaryl ring, optionally substituted with one or more substituents selected from the group consisting of lower alkyl, lower alkylene, halogen, perhaloalkyl, nitro, amino, cyano, amido, and ester; and c) $R_{10}$ is selected from the group consisting of hydrogen and lower alkyl d) $R_{11}$ is selected from the group consisting of:

i) hydrogen, alkyl, alkoxy, alkylene, and a five-membered or six-membered heteroaryl ring or a six-membered aryl or heteroaryl ring, optionally substituted with one or more substituents selected from the group consisting of lower alkyl, lower alkylene, halogen, perhaloalkyl, nitro, amino, cyano, amido, and ester;

ii) COY wherein Y is $C_1$-$C_8$ alkyl, $C_1$-$C_8$ alkoxy or $NR_{13}R_{14}$, wherein $R_{13}$ is hydrogen or $C_1$-$C_8$ alkyl and $R_{14}$ is hydrogen, $C_1$-$C_8$ alkyl, or $C_1$-$C_{14}$ phenalkyl;

iii) X or COX wherein X is

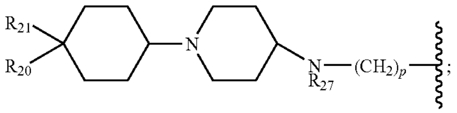

iv) halogen, $CF_3$, cyano, nitro, $COONHR_{25}$, $COON(R_{25})_2$, $COOSO_2R_{28}$, $COONR_{25}SO_2N(R_{25})_2$, $CO_2R_{25}$, $COON(R_{25})_2$, $COOSO_2N(R_{25})_2$, $COOSO_2R_{28}$.

v) $CONR_{15}R_{16}$, wherein $R_{15}$ is selected from the group consisting of hydrogen, alkyl cycloalkyl, aryl, or arylalkyl and $R_{16}$ is selected from the group consisting of hydrogen, alkyl cycloalkyl, aryl, or halosubstituted alkyl or $R_{15}$ and $R_{16}$ taken together with the nitrogen atom to which they are attached form 1-pyrrolidinyl, 1-piperidinyl, 1-azepinyl, 4-morpholinyl, 4-thiamorpholinyl, 1-piperazinyl, 4-diarylalkyl-1-piperazinyl, each of which is optionally substituted with one or more substituents selected from the group consisting of alkyl alkoxy, alkylthio, halo, trifloromethyl, or hydroxy;

vi) Z, COOZ, or C(O)(NH)Z, wherein Z is selected from the group consisting of

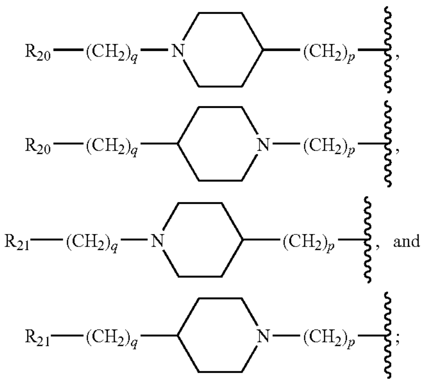

wherein

A) p and q are each independently 0-10;

B) $R_{20}$ is phenyl optionally substituted with one or more substituents independently selected from the group consisting of halogen, $CF_3$, cyano, nitro, $N(R_{25})_2$, $NR_{25}CONR_{27}$, $NR_{25}CON(R_{27})_2$, $NR_{25}SO_2R_{28}$, $NR_{25}SO_2N(R_{27})_2$, $(CH_2)_{0-4}CO_2R_{25}$, $(CH_2)_{0-4}CON(R_{25})_2$, $(CH_2)_{0-4}SO_2N(R_{25})_2$, $(CH_2)_{0-4}SO_2R_{28}$, and $C_{1-4}$ alkyl;

C) $R_{21}$ is selected from the group consisting of hydrogen, cyano, $OR_{28}$, $COOR_{25}$, $CON(R_{25})_2$, and phenyl optionally substituted with one or more substituents independently selected from the group consisting of halogen, $CF_3$, cyano, nitro, $N(R_{25})_2$, $NR_{25}CONR_{27}$, $NR_{25}CON(R_{27})_2$, $NR_{25}SO_2R_{28}$, $NR_{25}SO_2N(R_{27})_2$, $(CH_2)_{0-4}CO_2R_{25}$, $(CH_2)_{0-4}CON(R_{25})_2$, $(CH_2)_{0-4}SO_2N(R_{25})_2$, $(CH_2)_{0-4}SO_2R_{28}$, and $C_{1-4}$ alkyl;

D) $R_{25}$ and $R_{27}$ are each independently selected from hydrogen, $C_{1-8}$ alkyl, $C_{3-8}$ cycloalkyl, $(CH_2)_{0-4}CF_3$; and E) $R_{28}$ is selected from the group consisting of hydrogen, $C_{1-8}$ alkyl, $C_{3-8}$ cycloalkyl, and $(CH_2)_{0-4}CF_3$;

e) X is oxygen or sulfur; and f) Q is oxygen or nitrogen; provided that when Q is oxygen $R_3$ does not exist.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

The term "ester" refers to a chemical moiety with formula $-(R)_n-COOR'$, where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula $-(R)_n-C(O)NHR'$ or $-(R)_n-NHC(O)R'$, where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end is known to those of skill in the art and can readily be found in reference sources such as Greene and Wuts, Protective Groups in Organic Synthesis, 3rd Ed., John Wiley & Sons, New York, N.Y., 1999, which is incorporated herein by reference in its entirety.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

As used herein, the term "alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The alkyl group may have 1 to 40 carbon atoms (whenever it appears herein, a numerical range such as "1 to 40" refers to each integer in the given range; e.g. "1 to 40 carbon atoms" means that the alkyl group may consist of 1 carbon atom, 2 carbon atoms, 3 carbon atoms, etc., up to and including 40 carbon atoms, although the present definition also covers the occurrence of the term "alkyl" where no numerical range is designated). The alkyl group may also be a medium size alkyl having 1 to 20 carbon atoms. The alkyl group could also be a lower alkyl having 1 to 5 carbon atoms. The alkyl group of the compounds of the invention may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substituent may be substituted with one of the above substituents.

The substituent "R" appearing by itself and without a number designation refers to a substituent selected from the group consisting of alkyl, cycloalkyl, aryl, heteroaryl (bonded through a ring carbon) and heteroalicyclic (bonded through a ring carbon).

An "O-carboxy" group refers to a $RC(=O)O-$ group, where R is as defined herein.

A "C-carboxy" group refers to a $-C(=O)OR$ groups where R is as defined herein.

An "acetyl" group refers to a $-C(=O)CH_3$, group.

A "trihalomethanesulfonyl" group refers to a $X_3CS(=O)_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a $—S(=O)_2NR$, group, with R as defined herein.

A "N-sulfonamido" group refers to a $RS(=O)_2NH$— group with R as defined herein.

A "trihalomethanesulfonamido" group refers to a $X_3CS(=O)_2NR$— group with X and R as defined herein.

An "O-carbamyl" group refers to a —OC(=O)—NR, group-with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-amido" group refers to a $—C(=O)—NR_2$ group with R as defined herein.

An "N-amido" group refers to a RC(=O)NH— group, with R as defined herein.

The term "perhaloalkyl" refers to an alkyl group where all of the hydrogen atoms are replaced by halogen atoms. The term "halogen" comprises fluorine, chlorine, bromine, and iodine.

Unless otherwise indicated, when a substituent is deemed to be "optionally substituted," it is meant that the substitutent is a group that may be substituted with one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

In certain embodiments, $R_1$ is hydrogen or optionally substituted lower alkyl. In some of these embodiments, $R_1$ is selected from the group consisting of methyl, ethyl, n-propyl, isopropyl, n-butyl, sec-butyl, tert-butyl, and pentyl. Some embodiments include those in which $R_1$ is methyl or ethyl.

In other embodiments, $R_1$ is

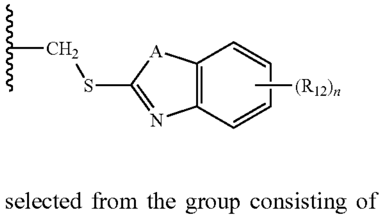

where A is selected from the group consisting of oxygen, sulfur, and —NH and $R_{12}$ is selected from the group consisting of hydrogen, hydroxy, alkoxy, haloalkoxy, halogen, haloalkyl, perhaloalkyl, nitro, amino, and a diazo salt, and n is between 0-4.

While in some embodiments A is oxygen, in other embodiments A is sulfur, and in still other embodiments A is —NH. In certain embodiments $R_{12}$ is hydrogen.

In some embodiments, $R_2$ and $R_3$ are each independently hydrogen or lower alkyl. In some of these embodiments, $R_2$ and $R_3$ may each be independently selected from the group consisting of methyl, ethyl, n-propyl, isopropyl, n-butyl, sec-butyl, tert-butyl, and pentyl.

In certain embodiments, $R_5$ is hydrogen or lower alkyl. In some of these embodiments $R_5$ may be selected from the group consisting of methyl, ethyl, n-propyl, isopropyl, n-butyl, sec-butyl, tert-butyl, and pentyl.

Embodiments of the present invention include compounds of Formula I, in which $R_6$-$R_8$ are each independently hydrogen or lower alkyl. In some embodiments $R_9$ is hydrogen or alkyl. When $R_9$ is alkyl, it may be a straight chain alkyl or a branched alkyl. In either case, $R_9$ may comprise at least 30 carbon atoms, at least 20 carbon atoms, at least 15 carbon atoms, or at least 10 carbon atoms. Thus, $R_9$ may be a pentadecyl ($C_{15}H_{31}$) group, a dodecyl ($C_{12}H_{25}$) group, or a decyl ($C_{10}H_{21}$) group.

In some embodiments, $R_{10}$ is hydrogen.

In certain embodiments, $R_{11}$ may be selected from the group consisting of hydrogen, alkyl, and alkoxy. When $R_{11}$ is alkoxy, it may be selected from the group consisting of methoxy, ethoxy, and propoxy.

In some embodiments, $R_{11}$ is COY, where Y is as defined herein. In certain of these embodiments Y is $C_1$-$C_8$ alkyloxy or $NR_{13}R_{14}$, where $R_{13}$ is hydrogen or $C_1$-$C_8$ alkyl and $R_{14}$ is hydrogen, $C_1$-$C_8$ alkyl, or $C_1$-$C_{14}$ phenalkyl. A "phenalkyl" group is one in which an optionally substituted phenyl group is attached to an alkyl substituent. Thus, $C_6H_5—CH_2$— is a $C_1$ phenalkyl group. The phenyl group may be substituted as set forth herein.

In certain embodiments, Y may be a $C_1$-$C_4$ alkyloxy, which may be an ethoxy. In other embodiments Y may be $NR_{13}R_{14}$, where $R_{13}$ and $R_{14}$ may each be independently $C_1$-$C_8$ alkyl. In some of these embodiments $R_{13}$ and $R_{14}$ are each methyl.

In some embodiments, $R_{11}$ is selected from the group consisting of, $COONHR_{25}$, $COON(R_{25})_2$, $COOSO_2R_{28}$, $COONR_{25}SO_2N(R_{25})_2$, $CO_2R_{25}$, $COON(R_{25})_2$, $COOSO_2N(R_{25})_2$, and $COOSO_2R_{28}$.

In other embodiments, $R_{11}$ is X or COX, as X is defined herein, while in still other embodiments, $R_{11}$ is Z, COOZ, or C(O)(NH)Z, as Z is defined herein. When $R_{11}$ comprises the X substituent, p may be 0-8, 0-5, 0-3, or 0-2. In some embodiments p is 0, while in other embodiments p is 2. When $R_{11}$ comprises the Z substituent, p and q may each independently be 0-8, 0-5, 0-3, or 0-2. In some embodiments p and q are each independently 0, while in other embodiments p and q are each independently 2.

Whether $R_{11}$ comprises the X substituent or the Z substituent, $R_{20}$ is phenyl optionally substituted with one or more substituents independently selected from the group consisting of halogen, $CF_3$, cyano, nitro, $N(R_{25})_2$, $NR_{25}CONR_{27}$, $NR_{25}CON(R_{27})_2$, $NR_{25}SO_2R_{28}$, $NR_{25}SO_2N(_{27})_2$, $(CH_2)_{0-4}CO_2R_{25}$, $(CH_2)_{0-4}CON(R_{25})_2$, $(CH_2)_{0-4}SO_2N(R_{25})_2$, $(CH_2)_{0-4}SO_2R_{28}$, and $C_{1-4}$ alkyl. In some embodiments the phenyl is unsubstituted, while in other embodiments it is substituted. In certain of these embodiments, the phenyl is substituted with halogen, which may be a fluorine. In other embodiments the phenyl is substituted with $(CH_2)_{0-4}CO_2R_{25}$. In some of these latter embodiments, the phenyl may be substituted with $—COOCH_3$.

In certain embodiments Q is nitrogen. In some of these embodiments the moiety $—C(O)QR_2R_3$ may be $—C(O)NH_2$. In other embodiments Q is oxygen, in which case it is singly substituted and $R_3$ does not exist.

Thus, some of the compounds of the above invention are listed in Table 1.

TABLE 1

| Number | Name |
|---|---|
| PPK-21 | 5-ethoxycarbonyl-4-(2-ethoxy-6-pentadecylphenyl)-6-(2'-mercapto-1'H-benzimidazolyl) methyl-3,4-dihydropyrimidin-2(1H)-one |
| PPK-22 | 5-ethoxycarbonyl-4-(2-methoxy-6-pentadecylphenyl)-6-methyl-3,4-dihydropyrimidin-2(1H)-one |
| PPK-23 | 5-methoxycarbonyl-4-(2-ethoxy-6-pentadecylphenyl)-6-methyl-3,4-dihydropyrimidin-2(1H)-one |
| PPK-24 | 5-methoxycarbonyl-4-(2-methoxy-6-pentadecylphenyl)-6-methyl-3,4-dihydropyrimidin-2(1H)-one |
| PPK-25 | 5-ethoxycarbonyl-4-(2-ethoxy-6-pentadecylphenyl)-6-methyl-3,4-dihydropyrimidin-2(1H)-one |
| PPK-26A | 5-methoxycarbonyl-4-(2-methoxy-6-(8' Z, 11' Z, 14' Z) pentadecatrienyl phenyl)-6-methyl-3,4-dihydropyrimidin-2(1H)-one |
| PPK-26B | 5-methoxycarbonyl-4-(2-methoxy-6-(8' Z, 11' Z) pentadecadienyl phenyl)-6-methyl-3,4-dihydropyrimidin-2(1H)-one |
| PPK-26C | 5-methoxycarbonyl-4-(2-methoxy-6-(8' Z) pentadecenyl phenyl)-6-methyl-3,4-dihydropyrimidin-2(1H)-one |
| PPK-27A | 5-ethoxycarbonyl-4-(2-ethoxy-6-(8' Z, 11' Z, 14' Z) pentadecatrienyl phenyl)-6-methyl-3,4-dihydropyrimidin-2(1H)-one |
| PPK-27B | 5-ethoxycarbonyl-4-(2-ethoxy-6-(8' Z, 11' Z) pentadecadienyl phenyl)-6-methyl-3,4-dihydropyrimidin-2(1H)-one |
| PPK-27C | 5-ethoxycarbonyl-4-(2-ethoxy-6-(8' Z) pentadecenyl phenyl)-6-methyl-3,4-dihydropyrimidin-2(1H)-one |
| PPK-28A | 5-methoxycarbonyl-4-(2-ethoxy-6-(8' Z, 11' Z, 14' Z) pentadecatrienyl phenyl)-6-methyl-3,4-dihydropyrimidin-2(1H)-one |
| PPK-28B | 5-methoxycarbonyl-4-(2-ethoxy-6-(8' Z, 11' Z) pentadecadienyl phenyl)-6-methyl-3,4-dihydropyrimidin-2(1H)-one |
| PPK-28C | 5-methoxycarbonyl-4-(2-ethoxy-6-(8' Z) pentadecenyl phenyl)-6-methyl-3,4-dihydropyrimidin-2(1H)-one |
| PPK-29A | 5-isopropoxycarbonyl-4-(2-ethoxy-6-(8' Z, 11' Z, 14' Z) pentadecatrienyl phenyl)-6-methyl-3,4-dihydropyrimidin-2(1H)-one |
| PPK-29B | 5-isopropoxycarbonyl-4-(2-ethoxy-6-(8' Z, 11' Z) pentadecadienyl phenyl)-6-methyl-3,4-dihydropyrimidin-2(1H)-one |
| PPK-29C | 5-isopropoxycarbonyl-4-(2-ethoxy-6-(8' Z) pentadecenyl phenyl)-6-methyl-3,4-dihydropyrimidin-2(1H)-one |
| PPK-30 | 3,6-dihydro-4-methyl-6-[2-methoxy-6-pentadecylphenyl]-2-oxo-1,5-(2H)-pyrimidinedicarboxylic acid 1-ethyl 5-methyl diester |
| PPK-31 | 3,6-dihydro-4-methyl-6-[2-methoxy-6-pentadecylphenyl]-2-oxo-1,5-(2H)-pyrimidinedicarboxylic acid bis (ethyl ester) |
| PPK-32 | 3,6-dihydro-4-methyl-6-[2-methoxy-6-pentadecylphenyl]-2-oxo-1,5-(2H)-pyrimidinedicarboxylic acid 1-ethyl 5-isopropyl diester |
| PPK-33 | 3,6-dihydro-4-methyl-6-[2-ethoxy-6-pentadecylphenyl]-2-oxo-1,5-(2H)-pyrimidinedicarboxylic acid 1-ethyl 5-methyl diester |
| PPK-34 | 3,6-dihydro-4-methyl-6-[2-ethoxy-6-pentadecylphenyl]-2-oxo-1,5-(2H)-pyrimidinedicarboxylic acid 1,5-diethyl diester |
| PPK-35 | 3,6-dihydro-4-methyl-6-[2-ethoxy-6-pentadecylphenyl]-2-oxo-1,5-(2H)-pyrimidinedicarboxylic acid 1-ethyl 5-isopropyl diester |
| PPK-36 | 3,6-dihydro-4-methyl-6-[2-isopropoxy-6-pentadecylphenyl]-2-oxo-1,5-(2H)-pyrimidinedicarboxylic acid 1-ethyl 5-methyl diester |
| PPK-37 | 3,6-dihydro-4-methyl-6-[2-isopropoxy-6-pentadecylphenyl]-2-oxo-1,5-(2H)-pyrimidinedicarboxylic acid 1,5-diethyl diester |
| PPK-38 | 3,6-dihydro-4-methyl-6-[2-isopropoxy-6-pentadecylphenyl]-2-oxo-1,5-(2H)-pyrimidinedicarboxylic acid 1-ethyl, 5-isopropyl diester |
| PPK-41 | 3,6-dihydro-4-methyl-6-(2-methoxy-6-pentadecylphenyl)-2-thioxo-1,5(2H)-pyrimidine dicarboxylic acid bis (ethyl ester) |
| PPK-42 | 3,6-dihydro-4-methyl-6-(2-ethoxy-6-pentadecylphenyl)-2-thioxo-1,5(2H)-pyrimidine dicarboxylic acid bis (ethyl ester) |
| PPK-43 | 3,6-dihydro-4-methyl-6-(2-isopropoxy-6-pentadecylphenyl)-2-thioxo-1,5(2H)-pyrimidine dicarboxylic acid bis (ethyl ester) |
| PPK-44 | 3,6-dihydro-4-methyl-6-(2-methoxy-6-dodecylphenyl)-2-thioxo-1,5(2H)-pyrimidine dicarboxylic acid bis (ethyl ester) |
| PPK-45 | 3,6-dihydro-4-methyl-6-(2-ethoxy-6-dodecylphenyl)-2-thioxo-1,5(2H)-pyrimidine dicarboxylic acid bis (ethyl ester) |
| PPK-46 | 3,6-dihydro-4-methyl-6-(2-isopropoxy-6-dodecylphenyl)-2-thioxo-1,5(2H)-pyrimidine dicarboxylic acid bis (ethyl ester) |
| PPK-47 | 3,6-dihydro-4-methyl-2-thioxo-6-[2-isopropoxy-6-pentadecylphenyl]-1,5(2H)-pyrimidine dicarboxylic acid 5-ethyl1-[1-(phenylmethyl)-4-piperidinyl]ester mono hydrochloride |
| PPK-48 | 3,6-dihydro-4-methyl-2-thioxo-6-[2-ethoxy-6-pentadecylphenyl]-1,5(2H)-pyrimidine dicarboxylic acid 5-ethyl1-[1-(phenylmethyl)-4-piperidinyl]ester mono hydrochloride |
| PPK-49 | 1,2,3,4-tetrahydro-6-methyl-4-[2-methoxy-6-pentadecylphenyl]-3-(1-oxo-propyl)2-thioxo-5-pyrimidine carboxylic acid ethyl ester |
| PPK-50 | 1,2,3,4-tetrahydro-6-methyl-4-[2-ethoxy-6-pentadecylphenyl]-3-(1-oxo-propyl)2-thioxo-5-pyrimidine carboxylic acid ethyl ester |

TABLE 1-continued

| Number | Name |
| --- | --- |
| PPK-51 | 1,2,3,4-tetrahydro-6-methyl-4-[2-isopropoxy-6-pentadecylphenyl]-3-(1-oxo-propyl)2-thioxo-5-pyrimidine carboxylic acid ethyl ester |
| PPK-52 | 1-[(dimethyl amino)carbonyl]-1,2,3,6-tetrahydro-4-methyl-6-[2-methoxy-6-pentadecylphenyl]-2-thioxo-5-pyrimidine carboxylic acid ethyl ester |
| PPK-53 | 1-[(dimethyl amino)carbonyl]-1,2,3,6-tetrahydro-4-methyl-6-[2-ethoxy-6-pentadecylphenyl]-2-thioxo-5-pyrimidine carboxylic acid ethyl ester |
| PPK-54 | 1-[(dimethyl amino)carbonyl]-1,2,3,6-tetrahydro-4-methyl-6-[2-isopropoxy-6-pentadecylphenyl]-2-thioxo-5-pyrimidine carboxylic acid ethyl ester |
| PPK-55 | 3,6-dihydro-4-methyl-2-thioxo-6-[2-methoxy-6-pentadecylphenyl)]-1,5 (2H)-pyrimidinedicarboxylic acid, 5-ethyl-1-[1-(phenmethyl)-4-piperidinyl] ester, monohydrochloride |
| PPK-56 | 3,6-dihydro-4-methyl-2-thioxo-6-[2-methoxy-6-pentadecylphenyl)]-1,5(2H)-pyrimidinedicarboxylic acid, 5-(1-methylethyl)1-[1-(phenmethyl)-4-piperidinyl] ester, monohydrochloride |
| PPK-57 | 3,6-dihydro-4-methyl-2-thioxo-6-[2-ethoxy-6-pentadecylphenyl]-1,5(2H)-pyrimidinedicarboxylic acid, 5-(1-methylethyl) 1-[1-(phenylmethyl)-4-piperidinyl] ester, monohydrochloride |
| PPK-58 | 3,6-dihydro-4-methyl-2-thioxo-6-[2-ethoxy-3,5-dinitro-6-pentadecylphenyl]-1,5(2H)-pyrimidinedicarboxylic acid, 5-(1-methylethyl) 1-[1-(phenylmethyl)-4-piperidinyl] ester, monohydrochloride |
| PPK-59 | 1,2,3,6-Tetrahydro-4-methyl-1-[3-[methyl(phenylmethyl)amino]propyl]-2-thioxo-6-[2-methoxy-6-pentadecylphenyl]-5-pyrimidinecarboxylic acid, 1-methylethyl ester, monohydrochloride |
| PPK-60 | 1,2,3,6-Tetrahydro-4-methyl-1-[2-[1-(phenylmethyl)-4-piperidinyl]ethyl]-2-thioxo-6-[2-methoxy-6-pentadecylphenyl)-5-pyrimidinecarboxylic acid, 1-methylethyl ester, monohydrochloride |
| PPK-61 | 3,6-dihydro-4-methyl-2-thioxo-6-[2-ethoxy-6-pentadecylphenyl]-1,5(2H)-pyrimidinedicarboxylic acid, 1-[1-[(4-florophenyl)methyl]-4-piperidinyl] 5-(1-methylethyl) ester, monohydrochloride |
| PPK-62 | 4-ethyl-5-methoxycarbonyl-1-{N-[3[4-(4-methoxycarbonyl)-4-phenylpiperidin-1-yl]propyl]carboxamido}-6-[2-methoxy-6-pentadecylphenyl]-2-oxo-1,2,3,6-tetrahydropyrimidine |
| PPK-63 | 4-ethyl-5-methoxycarbonyl-1-{N-[3[4-(4-methoxycarbonyl)-4-phenylpiperidin-1-yl]propyl]carboxamido}-6-[2-ethoxy-6-pentadecylphenyl]-2-oxo-1,2,3,6-tetrahydropyrimidine |
| PPK-64 | 5-carboxamido-4-ethyl-1-{N-[-[3-(4-methoxycarbonylphenylpiperidin-1-yl)-propyl]carboxamido}-6-[2-methoxy-6-pentadecylphenyl]-2-oxo-1,2,3,6-tetrahydropyrimidine |
| PPK-65 | 4-ethyl-5-(N-methylcarboxamido)-1-{N-[3-(4-methoxycarbonylphenylpiperidin-1-yl)propyl]carboxamido}-6-[2-methoxy-6-pentadecylphenyl]-2-oxo-1,2,3,6-tetrahydropyrimidine |
| PPK-66 | 5-methoxycarbonyl-1-{N-[3-[4-(4-methoxycarbonyl)-4-phenylpiperidin-1-yl]propyl]carboxamido}-4-methyl-6-[2-methoxy-6-pentadecylphenyl]-2-oxo-1,2,3,6-tetrahydropyrimidine |
| PPK-67 | 5-ethoxycarbonyl-1-{N-[3-[4-(4-methoxycarbonyl)-4-phenylpiperidin-1-yl]propyl]carboxamido}-4-methyl-6-[2-methoxy-6-pentadecylphenyl]-2-oxo-1,2,3,6-tetrahydropyrimidine |
| PPK-68 | 5-carboxamido-1-{N-[3-[4-(4-methoxycarbonyl)-4-phenylpiperidin-1-yl]propyl]carboxamido}-4-methyl-6-[2-methoxy-6-pentadecylphenyl]-2-oxo-1,2,3,6-tetrahydropyrimidine |
| PPK-69 | 1-{N-[3-[4-(4-methoxycarbonyl)-4-phenylpiperidin-1-yl]propyl]carboxamido}-4-methyl-5-(N-methylcarboxamido)-6-[2-methoxy-6-pentadecylphenyl]-2-oxo-1,2,3,6-tetrahydropyrimidine |

The structures of the above compounds are shown in Table 2. The substituent designation for Table 2 refers to the substituents of Formula II.

TABLE 2

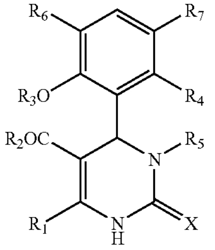

(II)

| Number | $R_1$ | $R_2$ | $R_3$ | $R_4$ | $R_5$ | $R_6$ | $R_7$ | X |
|---|---|---|---|---|---|---|---|---|
| PPK-21 | 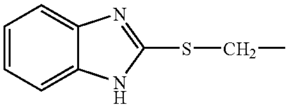 | ethoxy | ethyl | $C_{15}H_{31}$ | H | H | H | O |
| PPK-22 | methyl | ethoxy | ethyl | $C_{15}H_{31}$ | H | H | H | O |
| PPK-23 | methyl | methoxy | ethyl | $C_{15}H_{31}$ | H | H | H | O |
| PPK-24 | methyl | methoxy | methyl | $C_{15}H_{31}$ | H | H | H | O |
| PPK-25 | methyl | ethoxy | ethyl | $C_{15}H_{31}$ | H | H | H | O |
| PPK-26A | methyl | methoxy | methyl | (8'Z, 11'Z, 14'Z) pentadecatrienyl | H | H | H | O |
| PPK-26B | methyl | methoxy | methyl | (8'Z, 11'Z) pentadecadienyl | H | H | H | O |
| PPK-26C | methyl | methoxy | methyl | (8'Z) pentadecenyl | H | H | H | O |
| PPK-27A | methyl | ethoxy | ethyl | (8'Z, 11'Z, 14'Z) pentadecatrienyl | H | H | H | O |
| PPK-27B | methyl | ethoxy | ethyl | (8'Z, 11'Z) pentadecadienyl | H | H | H | O |
| PPK-27C | methyl | ethoxy | ethyl | (8'Z) pentadecenyl | H | H | H | O |
| PPK-28A | methyl | methoxy | ethyl | (8'Z, 11'Z, 14'Z) pentadecatrienyl | H | H | H | O |
| PPK-28B | methyl | methoxy | ethyl | (8'Z, 11'Z) pentadecadienyl | H | H | H | O |
| PPK-28C | methyl | methoxy | ethyl | (8'Z) pentadecenyl | H | H | H | O |
| PPK-29A | methyl | isopropoxy | ethyl | (8'Z, 11'Z, 14'Z) pentadecatrienyl | H | H | H | O |
| PPK-29B | methyl | isopropoxy | ethyl | (8'Z, 11'Z) pentadecadienyl | H | H | H | O |
| PPK-29C | methyl | isopropoxy | ethyl | (8'Z) pentadecenyl | H | H | H | O |
| PPK-30 | methyl | methoxy | methyl | $C_{15}H_{31}$ | ethyl | H | H | O |
| PPK-31 | methyl | ethoxy | methyl | $C_{15}H_{31}$ | ethyl | H | H | O |
| PPK-32 | methyl | isopropoxy | methyl | $C_{15}H_{31}$ | ethyl | H | H | O |
| PPK-33 | methyl | methoxy | ethyl | $C_{15}H_{31}$ | ethyl | H | H | O |
| PPK-34 | methyl | ethoxy | ethyl | $C_{15}H_{31}$ | ethyl | H | H | O |
| PPK-35 | methyl | isopropoxy | ethyl | $C_{15}H_{31}$ | ethyl | H | H | O |
| PPK-36 | methyl | methoxy | isopropyl | $C_{15}H_{31}$ | ethyl | H | H | O |
| PPK-37 | methyl | ethoxy | isopropyl | $C_{15}H_{31}$ | ethyl | H | H | O |
| PPK-38 | methyl | isopropoxy | isopropyl | $C_{15}H_{31}$ | ethyl | H | H | O |
| PPK-41 | methyl | ethoxy | methyl | $C_{15}H_{31}$ | COOEt | H | H | S |
| PPK-42 | methyl | ethoxy | ethyl | $C_{15}H_{31}$ | COOEt | H | H | S |
| PPK-43 | methyl | ethoxy | isopropyl | $C_{15}H_{31}$ | COOEt | H | H | S |
| PPK-44 | methyl | ethoxy | methyl | $C_{12}H_{25}$ | COOEt | H | H | S |
| PPK-45 | methyl | ethoxy | ethyl | $C_{12}H_{25}$ | COOEt | H | H | S |
| PPK-46 | methyl | ethoxy | isopropyl | $C_{12}H_{25}$ | COOEt | H | H | S |
| PPK-47 | methyl | ethoxy | isopropyl | $C_{15}H_{31}$ | A* | H | H | S |
| PPK-48 | methyl | ethoxy | ethyl | $C_{15}H_{31}$ | A* | H | H | S |
| PPK-49 | methyl | ethoxy | methyl | $C_{15}H_{31}$ | $—OC_3H_7$ | H | H | S |
| PPK-50 | methyl | ethoxy | ethyl | $C_{15}H_{31}$ | $—OC_3H_7$ | H | H | S |
| PPK-51 | methyl | ethoxy | isopropyl | $C_{15}H_{31}$ | $—OC_3H_7$ | H | H | S |
| PPK-52 | methyl | ethoxy | methyl | $C_{15}H_{31}$ | $CONMe_2$ | H | H | S |
| PPK-53 | methyl | ethoxy | ethyl | $C_{15}H_{31}$ | $CONMe_2$ | H | H | S |
| PPK-54 | methyl | ethoxy | isopropyl | $C_{15}H_{31}$ | $CONMe_2$ | H | H | S |
| PPK-55 | methyl | ethoxy | methyl | $C_{15}H_{31}$ | A | H | H | S |

TABLE 2-continued (II)

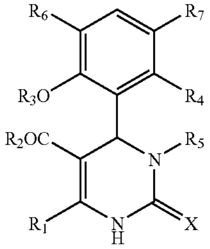

| Number | $R_1$ | $R_2$ | $R_3$ | $R_4$ | $R_5$ | $R_6$ | $R_7$ | X |
|---|---|---|---|---|---|---|---|---|
| PPK-56 | methyl | isopropoxy | methyl | $C_{15}H_{31}$ | A | H | H | S |
| PPK-57 | methyl | isopropoxy | ethyl | $C_{15}H_{31}$ | A | H | H | S |
| PPK-58 | methyl | isopropoxy | ethyl | $C_{15}H_{31}$ | A | $—NO_2$ | $—NO_2$ | S |
| PPK-59 | methyl | isopropoxy | methyl | $C_{15}H_{31}$ | B | H | H | S |
| PPK-60 | methyl | isopropoxy | methyl | $C_{15}H_{31}$ | C | H | H | S |
| PPK-61 | methyl | isopropoxy | ethyl | $C_{15}H_{31}$ | D | H | H | S |
| PPK-62 | ethyl | methoxy | methyl | $C_{15}H_{31}$ | E | H | H | O |
| PPK-63 | ethyl | methoxy | ethyl | $C_{15}H_{31}$ | E | H | H | O |
| PPK-64 | ethyl | $—NH_2$ | methyl | $C_{15}H_{31}$ | E | H | H | O |
| PPK-65 | ethyl | $—NH(CH_3)$ | methyl | $C_{15}H_{31}$ | E | H | H | O |
| PPK-66 | methyl | methoxy | methyl | $C_{15}H_{31}$ | E | H | H | O |
| PPK-67 | methyl | ethoxy | methyl | $C_{15}H_{31}$ | E | H | H | O |
| PPK-68 | methyl | $—NH_2$ | methyl | $C_{15}H_{31}$ | E | H | H | O |
| PPK-69 | methyl | $—NH(CH_3)$ | methyl | $C_{15}H_{31}$ | E | H | H | O |

A =

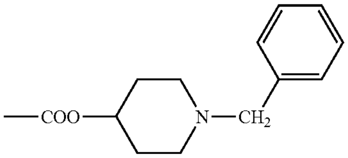

B = $—(CH_2)_3—N(CH_3)(CH_2C_6H_5)$

C =

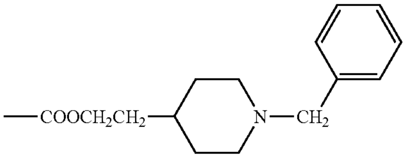

D =

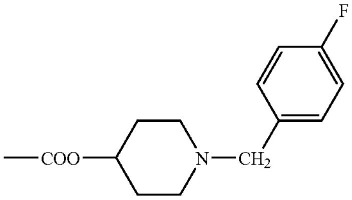

E =

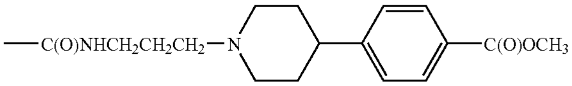

II. Methods of Treatment

In another aspect, the invention relates to a method of modulating the activity of a calcium channel in a cell comprising the step of contacting said cell with a compound of Formula I, as described above. The calcium channel being modulated may be a low voltage activated calcium channel or a high voltage activated calcium channel.

In a further aspect, the invention relates to a method of treating a disease associated with a cellular calcium channel comprising identifying a subject in need of such treatment, and administering to the subject a therapeutically effective amount of a compound of Formula I, as described above. In certain embodiments, the subject may be a mammal. The mammal may be selected from the group consisting of mice, rats, rabbits, guinea pigs, dogs, cats, sheep, goats, cows, primates, such as monkeys, chimpanzees, and apes, and humans. In some embodiments, the subject is a human. Embodiments of the invention include those in which the disease to be treated is a cardiovascular disease.

III. Pharmaceutical Compositions

In another aspect, the invention relates to a pharmaceutical composition comprising a compound of Formula I, as described above, and a physiologically acceptable carrier, diluent, or excipient, or a combination thereof.

The term "pharmaceutical composition" refers to a mixture of a compound of the invention with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The compounds described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

a) Routes of Administration

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly into a solid tumor, often in a depot or sustained release formulation. Furthermore, one may administer the drug in a targeted drug delivery system, for example, in a liposome coated with tumor-specific antibody. The liposomes will be targeted to and taken up selectively by the tumor.

b) Composition/Formulation

The pharmaceutical compositions of the present invention may be manufactured in a manner that is itself known, e.g. by means of conventional mixing, dissolving, granulating, dragee-making, levigating, emulsifying, encapsulating, entrapping or tabeleting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g. in Remington's Pharmaceutical Sciences, above.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with one or more compound of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g. dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

The compounds may be formulated for parenteral administration by injection, e.g. by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g. sterile pyrogen-free water, before use.

The compounds may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant Polysorbate 80™, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

c) Effective Dosage.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

For any compound used in the methods of the invention, the therapeutically effective dose can be estimated initially from cell culture assays. For example, a dose can be formulated in animal models to achieve a circulating concentration range that includes the $IC_{50}$ as determined in cell culture. Such information can be used to more accurately determine useful doses in humans.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient.

The daily dosage regimen for an adult human patient may be, for example, an oral dose of between 0.1 mg and 500 mg, preferably between 1 mg and 250 mg, e.g. 5 to 200 mg or an intravenous, subcutaneous, or intramuscular dose of between 0.01 mg and 100 mg, preferably between 0.1 mg and 60 mg, e.g. 1 to 40 mg of the compound of the formula (I) or a pharmaceutically acceptable salt thereof calculated as the free base, the compound being administered 1 to 4 times per day. Alternatively the compounds of the invention may be administered by continuous intravenous infusion, preferably at a dose of up to 400 mg per day. Thus, the total daily dosage by oral administration will be in the range 1 to 2000 mg and the total daily dosage by parenteral administration will be in the range 0.1 to 400 mg. Suitably the compounds will be administered for a period of continuous therapy, for example for a week or more.

Dosage amount and interval may be adjusted individually to provide plasma levels of the active moiety which are sufficient to maintain the modulating effects, or minimal effective concentration (MEC). The MEC will vary for each compound but can be estimated from in vitro data; e.g. the concentration necessary to achieve 50-90% of calcium channel blockage, using the assays known in the art. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

d) Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

IV. Synthesis of the Compounds of the Invention

The compounds of the present invention can be divided into two general categories: those with a substitution at a nitrogen (either position 1 or position 3) of the pyrimidine ring and those without any substitution at that point, i.e., where that position is occupied by —NH. Scheme 1, below, shows the synthetic procedure for synthesizing compounds without N-substitution.

Scheme 1

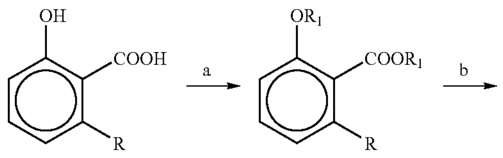

-continued

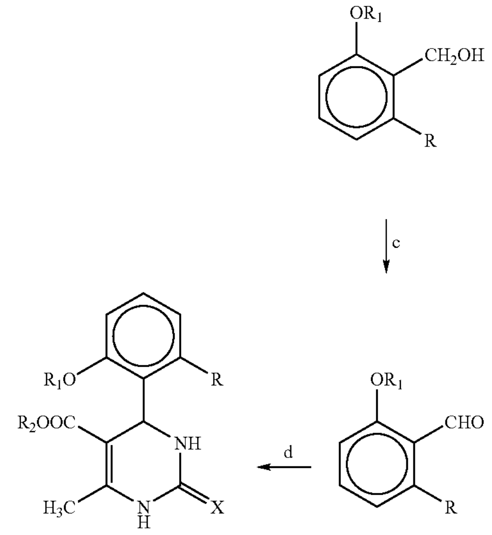

X = O, S
R = alkyl chain (as described in claims)

a. dialkyl sulphate, $K_2CO_3$, acetone, reflux 4 hrs
b. $LiAlH_4$, tetrahydrofuran, reflux, 3 hrs
c. pyridinium chloro chromate, dichloromethane, rt 3 hrs
d. appropriate acetoacetate, $BF_3 \cdot O(Et)_2$, (Urea or ThioUrea), tetrahydrofuran Scheme 2 shows the synthetic procedure for synthesizing compounds that are substituted at the ring nitrogen ortho to the phenyl group.

Scheme 2

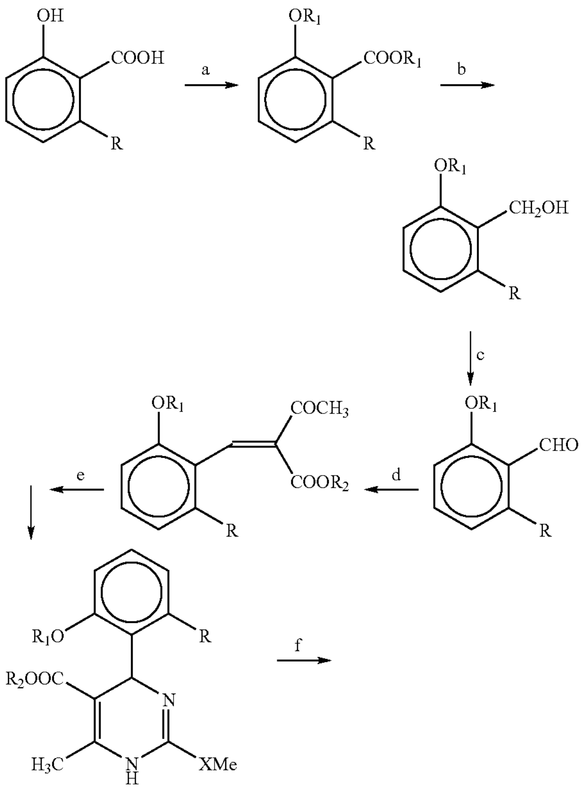

-continued

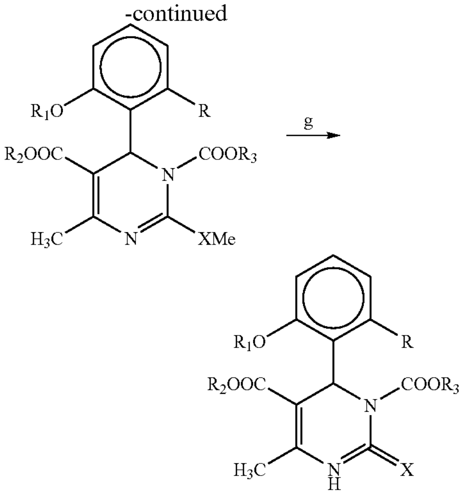

X = O, S
R = alkyl chain (as described in claims)

a. dialkyl sulphate, $K_2CO_3$, acetone, reflux 4 hrs
b. $LiAlH_4$, tetrahydrofuran, reflux, 3 hrs
c. pyridinium chloro chromate, dichloromethane, rt 3 hrs
d. appropriate acetoacetate, acetic acid, piperidine, isopropyl alcohol, rt 4-6 hrs
e. appropriately substituted urea or thiourea, sodium bicarbonate, dimethyl formamide, heat at 60° C. for 6-8 hrs
f. appropriately substituted chloroformate, pyridine, dichloromethane
g. pyridine, dichloromethane (for X—O)
g. trifloro acetic acid, ethane thiol, dichloromethane, rt 12 hrs (for X═S)

EXAMPLES

The examples below are illustrative of some of the embodiments of the invention only and should not be construed to limit the scope of the claims.

Example 1

Extraction of ene Mixture of Anacardic Acid (2-hydroxy-6-pentadecyl benzoic acid) from Solvent Extracted CNSL Commercially available solvent extracted cashew nut shell liquid (CNSL) (100 g) was dissolved in 5% aqueous methanol (600 mL). To the methanolic solution was added activated charcoal (20 g), stirred for 15 minutes, then filtered over celite bed to remove any insoluble material. The clear filtrate was transferred into three neck round bottom flask fitted with a double surface reflux condenser and mechanical stirrer. Calcium hydroxide (50 g) was added in portions at room temperature and the reaction mass temperature was raised to 50° C. and allowed to maintain for 3 hrs. Progress of the reaction was monitored by thin layer chromatography (TLC) using hexane-ethyl acetate (8:2) as mobile phase. After the completion of reaction, the precipitated calcium anacardate was filtered and washed thoroughly with methanol (200 mL). The resultant cake was dried under vacuum at 45-50° C. for 2 hrs to yield calcium anacardate (120 g).

Dry cake (120 g) was suspended in distilled water (440 mL), added concentrated hydrochloric acid (33%, 60 mL) and stirred for 1 hr. Resultant solution was extracted with ethylacetate (2×150 mL). The combined organic layer was washed with distilled water (2×500 mL), dried over anhydrous sodium sulfate and concentrated under reduced pressure to yield an ene mixture of anacardic acid. (Yield: 60 g).

Example 2

Hydrogenation of Anacardic Acid ene Mixture

Anacardic acid ene mixture (30 g,) was dissolved in methanol (120 ml). 5% Pd/C (0.75 g, 2.5%) was added slowly and this solution were transferred to 250-mL hydrogenation flask. Initially the solution was flushed with nitrogen and then with hydrogen. Hydrogenation was carried out with 2.5 kg/$cm^2$ hydrogen gas pressure for 2 hrs. Then the solution was filtered through a celite bed to obtain catalyst free solution. This was evaporated under vacuum to get crude saturated anacardic acid. It was then recrystallised from petroleum ether (Yield: 25 g).

Example 3

Synthesis of ethyl 2-ethoxy-6-pentadecyl-benzoate

Anacardic acid (10.11 g, 29 mmol) was dissolved in acetone (60 mL) and potassium carbonate (4.0 g, 29 mmol) was charged. Diethyl sulfate (8.93 g, 58 mmol) was added slowly under stirring. This solution was then transferred to a three-neck flask fitted with a reflux condenser and mechanical stirrer, and refluxed for 4 hrs. Progress of reaction was monitored by TLC (mobile phase: Hexane:EtOAc 9:1). After completion of reaction, it was filtered and acetone was evaporated under vacuum. Crude product was dissolved in dichloromethane (50 mL) and washed with water (2×50 mL), 5% sodium bicarbonate solution (50 mL), saturated brine (50 mL) and finally with distilled water (2×50 mL). The organic layer was dried over anhydrous sodium sulphate, and evaporated under vacuum to give ethyl 2-ethoxy-6-pentadecyl-benzoate as oil. This was then dissolved in minimum amount of petroleum ether (40-60° C.) and cooled to 0° C. to give light brownish crystals (Yield: 12 g).

Example 4

Synthesis of isopropyl 2-isopropoxy-6-pentadecyl-benzoate

Anacardic acid (10.11 g, 29 mmol) was dissolved in isobutyl methyl ketone (60 mL). To this, finely powdered potassium carbonate (4.0 g, 29 mmol) and benzyl tributyl ammonium chloride (1 g) was added. Slowly, isopropyl bromide (7.13 g, 58 mmol) was added and refluxed for 8 hrs. TLC was checked in hexane:EtOAc (9:1). Solution was filtered and evaporated under vacuum to give a viscous liquid. Crude product was dissolved in dichloromethane (50 mL) and washed with water (2×50 mL), 5% sodium bicarbonate solution (50 mL), saturated brine (50 mL) and finally with water (2×50 mL). The organic layer was dried over anhydrous sodium sulfate and evaporated under vacuum to give isopropyl 2-isopropoxy-6-pentadecyl-benzoate as oil (Yield: 12 g).

Example 5

Synthesis of 2-ethoxy-6-pentadecyl-benzyl alcohol

Ethyl 2-ethoxy-6-pentadecyl-benzoate (10.9 g, 27 mmol) was dissolved in dry tetrahydrofuran (60 mL). This solution was transferred to dry 250 mL three neck round bottom flask fitted with reflux condenser, mechanical stirrer and it was maintained under nitrogen atmosphere through out the reaction. To this lithium aluminum hydride (2.04 g, 54 mmol) was added slowly. Reaction was highly exothermic. After addition the solution was slowly brought to the reflux temperature and maintained at that temperature for about two hours and TLC was checked in hexane:EtOAc (8:2). After completion of reaction, excess lithium aluminium hydride was decomposed by drop-wise addition of ethylacetate (80 mL). To this 5 M HCl (100 mL) was added and organic layer was separated, dried over anhydrous sodium sulphate, concentrated under vacuum to give a light brownish solid. This was recrystallised from petroleum ether (40-60° C.) to give white solid. Yield: 8 g.

Example 6

Synthesis of 2-ethoxy-6-pentadecyl-benzaldehyde

To a 250 mL round bottom flask fitted with a reflux condenser, was added pyridinium chloro chromate (PCC) (16.1 g, 75 mmol) in anhydrous dichloromethane (100 mL). 2-Ethoxy-6-pentadecyl-benzyl alcohol (18.1 g, 50 mmol) in dichloromethane (10 mL) was added in one portion to the magnetically stirred solution. After 1.5 hr dry ether (100 mL) was added and the supernatant decanted from the black gum. The insoluble residue was washed thoroughly with diethyl ether (3×25 mL), where upon it became black granular solid. The organic solution was passed through a short pad of celite, and the solvent was removed by distillation to obtain brownish low melting solid (Yield: 15 g).

Example 7

Synthesis of 1,4-dihydro-2-[[(4-methoxyphenyl) methyl]thio]-6-methyl-4-[2-methoxy-6-pentadecylphenyl]-5-pyrimidinecarboxylic acid ethyl ester The reaction mixture containing 2-[[2-methoxy-6-pentadecyl phenyl]methylene]-3-oxobutanoic acid ethyl ester (3 g, 6.6 mmol), 2-((4-methoxyphenyl)methyl)-2-thiopseudourea hydrochloride (1.2 g, 6.6 mmol), and sodium acetate (0.6 g, 7 mmol) in dimethylformamide (30 mL) was heated at 70° C. for 4 h. The reaction was cooled to room temperature, diluted with ether, and filtered. The filtrate was washed with water, sodium bicarbonate, and brine and dried over anhydrous sodium sulfate. The solvent was evaporated, and the compound was obtained as brown viscous liquid.

Example 8

Synthesis of 1,4-dihydro-2-[[(4-methoxyphenyl) methyl)oxy]-6-methyl-4-[2-methoxy-6-pentadecylphenyl]-5-pyrimidinecarboxylic acid ethyl ester The reaction mixture containing 2-[[2-methoxy-6-pentadecyl phenyl]methylene]-3-oxobutanoic acid ethyl ester (3 g, 6.6 mmol), 2-((4-methoxyphenyl)methyl)-2-oxypseudourea hydrochloride (1.1 g, 6.6 mmol), and sodium acetate (0.6 g, 7 mmol) in dimethylformamide (30 mL) was heated at 70° C. for 4 h. The reaction was cooled to room temperature, diluted with ether, and filtered. The filtrate was washed with water, sodium bicarbonate, and brine and dried over anhydrous sodium sulfate. The solvent was evaporated, and the compound was obtained as brown viscous liquid.

Example 9

5-ethoxycarbonyl-4-(2-ethoxy-6-pentadecylphenyl)-6-(2'-mercapto-1'H-benzimidazolyl)methyl-3,4-dihydropyrimidin-2(1H)-one (PPK-21)

A solution of 4(2'-mercapto-1'H-benzimidazolyl)ethylacetoacetate (2.3 g, 8.3 mmol), 2-ethoxy-6-pentadecyl benzaldehyde (3 g, 8.3 mmol) and urea (1.0 g, 16.6 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography and recrystallised from hexane to get white crystalline solid of title compound.

Melting point: 87-88° C.

IR ($cm^{-1}$): 3425 (N—H), 2920 (C—H), 1694 (C═O)

Mass (Electrospray): 663 (M+1), 661 (M−1)

$^1H$ NMR (δ ppm): 8.5 (bs, 1H, $D_2O$ exchangeable, N—H) 7.7 (d, J=6 Hz, 1H, Aromatic proton) 7.5 (m, 1H, Aromatic proton) 7.25 (m, 3H, Aromatic proton, N—H, $D_2O$ exchangeable) 7.15 (t, J=8 Hz, 1H, Aromatic proton) 6.85 (d, J=8 Hz, 2H, Aromatic proton) 5.8 (s, 1H, $C_4$—H) 4.6 (s, 1H, $D_2O$ exchangeable, N—H) 4.5 (s, 2H, S—$CH_2$) 4.0 (m, J=6 Hz, 4H, O—$CH_2$) 3.1 (m, 1H, benzylic) 2.5 (m, 1H, benzylic) 1.85-1.1 (m, 35H, $(CH_2)_{13}$ from alkyl chain, $CH_3$, $CH_3$, allylic $CH_3$) 0.9 (dt, 3H, terminal $CH_3$ from alkyl chain).

Example 10

5-ethoxycarbonyl-4-(2-methoxy-6-pentadecylphenyl)-6-methyl-3,4-dihydropyrimidin-2(1H)-one (PPK-22)

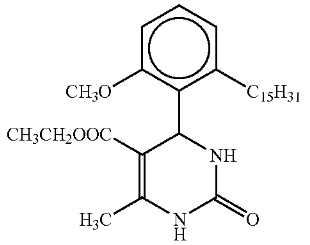

A solution of ethylacetoacetate (1.13 g, 8.6 mmol), 2-methoxy-6-pentadecyl benzaldehyde (3 g, 8.6 mmol) and urea (1.04 g, 17.3 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography and recrystallised from hexane to get white crystalline solid of title compound.

Melting point: 91-93° C.

IR ($cm^{-1}$): 3420 (N—H), 2922 (C—H), 1690 (C═O)

Mass (Electrospray): 501 (M+1), 499 (M−1)

$^1H$ NMR (δ ppm): 7.6 (bs, 1H, $D_2O$ exchangeable, N—H) 7.15 (t, J=8 Hz, 1H, aromatic proton) 6.85 (d, J=8 Hz, 2H, aromatic protons) 5.95 (s, 1H, $C_4$—H) 4.95 (s, 1H, $D_2O$ exchangeable, N—H) 4.0 (m, 2H, O—$CH_2$) 3.8 (s, 3H, O—$CH_3$) 3.15 (m, 1H, benzylic) 2.5 (m, 1H, benzylic) 2.25 (s, 3H, allylic) 1.85-0.95 (m, 29H, $(CH_2)_{13}$ from alkyl chain, $CH_3$) 0.9 (dt, 3H, terminal $CH_3$ from alkyl chain).

bs-broad singlet, t-triplet, d-doublet, s-singlet, m-multiplet, dt-distorted triplet.

Example 11

5-methoxycarbonyl-4-(2-ethoxy-6-pentadecylphenyl)-6-methyl-3,4-dihydropyrimidin-2(1H)-one (PPK-23)

A solution of methylacetoacetate (1.2 g, 8.5 mmol), 2-ethoxy-6-pentadecyl benzaldehyde (3 g, 8.5 mmol) and urea (1.00 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography and recrystallized from hexane to get white crystalline solid of title compound.

Melting point: 127-129° C.

IR ($cm^{-1}$): 3426 (N—H), 2920 (C—H), 1694 (C═O)

Mass (Electrospray): 501 (M+1), 499 (M−1)

$^1H$ NMR (δ ppm): 7.6 (bs, 1H, $D_2O$ exchangeable, N—H) 7.1 (t, J=8 Hz, 1H, aromatic proton) 6.72 (d, J=8 Hz, 2H, aromatic protons) 5.8 (s, 1H, $C_4$—H) 4.8 (s, 1H, $D_2O$ exchangeable, N—H) 4.0 (q, 2H, J=6 Hz, O—$CH_2$) 3.5 (s, 3H, O—$CH_3$) 3.1 (m, 1H, benzylic) 2.5 (m, 1H, benzylic) 2.3 (s, 3H, allylic) 1.8-1.1 (m, 29H, $(CH_2)_{13}$ from alkyl chain, $CH_3$) 0.85 (dt, 3H, terminal $CH_3$ from alkyl chain).

bs-broad singlet, t-triplet, d-doublet, s-singlet, m-multiplet, dt-distorted triplet, q-quartet.

Example 12

5-methoxycarbonyl-4-(2-methoxy-6-pentadecylphenyl)-6-methyl-3,4-dihydropyrimidin-2(1H)-one (PPK-24)

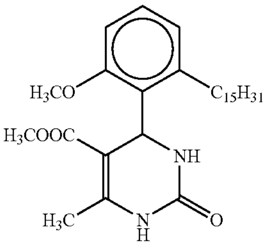

A solution of methylacetoacetate (1.2 g, 8.5 mmol), 2-methoxy-6-pentadecyl benzaldehyde (3.1 g, 8.5 mmol) and urea (1.00 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography and recrystallized from hexane to get white crystalline solid of title compound.

Melting point: 101-102° C.

IR ($cm^{-1}$): 3425 (N—H), 2918 (C—H), 1690 (C═O)

Mass (Electrospray): 487 (M+1), 485 (M−1)

$^1H$ NMR (δ ppm): 7.6 (bs, 1H, $D_2O$ exchangeable, N—H) 7.15 (t, J=8 Hz, 1H, aromatic proton) 6.73 (d, J=8 Hz, 2H, aromatic protons) 5.8 (s, 1H, $C_4$—H) 4.8 (s, 1H, $D_2O$ exchangeable, N—H) 3.78 (s, 3H, O—$CH_2$) 3.6 (s, 3H, O—$CH_3$) 3.1 (m, 1H, benzylic) 2.5 (m, 1H, benzylic) 2.3 (s, 3H, allylic) 1.8-1.1 (m, 26H, $(CH_2)_{13}$ from alkyl chain) 0.85 (dt, 3H, terminal $CH_3$ from alkyl chain).

bs-broad singlet, t-triplet, d-doublet, s-singlet, m-multiplet, dt-distorted triplet, q-quartet.

Example 13

5-ethoxycarbonyl-4-(2-ethoxy-6-pentadecylphenyl)-6-methyl-3,4-dihydropyrimidin-2(1H)-one (PPK-25)

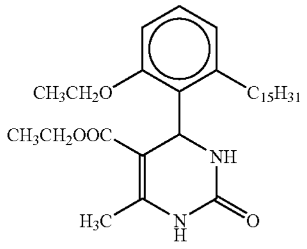

A solution of ethylacetoacetate (1.25 g, 8.5 mmol), 2-ethoxy-6-pentadecyl benzaldehyde (3 g, 8.5 mmol) and urea (1.1 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography and recrystallized from hexane to get white crystalline solid of title compound.

Melting point: 99-100° C.

IR ($cm^{-1}$): 3420 (N—H), 2924 (C—H), 1690 (C═O)

Mass (Electrospray): 515 (M+1), 513 (M−1)

$^1H$ NMR (δ ppm): 7.35 (bs, 1H, $D_2O$ exchangeable, N—H) 7.15 (t, J=8 Hz, 1H, aromatic proton) 6.72 (d, J=8 Hz, 2H, aromatic protons) 5.8 (s, 1H, $C_4$—H) 4.75 (s, 1H, $D_2O$ exchangeable, N—H) 4.0 (m, 4H, O—$CH_2$) 3.15 (m, 1H, benzylic) 2.45 (m, 1H, benzylic) 2.3 (s, 3H, allylic) 1.8-1.1 (m, 32H, $(CH_2)_{13}$ from alkyl chain, $CH_3$, $CH_3$) 0.9 (dt, 3H, terminal $CH_3$ from alkyl chain).

bs-broad singlet, t-triplet, d-doublet, s-singlet, m-multiplet, dt-distorted triplet Example 14

5-methoxycarbonyl-4-(2-methoxy-6-(8'Z,11'Z,14'Z) pentadecatrienyl phenyl)-6-methyl-3,4-dihydropyrimidin-2(1H)-one (PPK-26A)

A solution of methylacetoacetate (1.2 g, 8.5 mmol), 2-methoxy-6-(8'Z,11'Z,14'Z) pentadecatrienyl benzaldehyde (3.1 g, 8.5 mmol) and urea (1.00 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography and recrystallised from hexane to get white crystalline solid of title compound.

IR ($cm^{-1}$): 3427 (N—H), 2922 (C—H), 1691 (C═O)

Mass (Electrospray): 481 (M+1), 479 (M−1)

Example 15

5-methoxycarbonyl-4-(2-methoxy-6-(8'Z,11'Z) pentadecadienyl phenyl)-6-methyl-3,4-dihydropyrimidin-2(1H)-one (PPK-26B)

A solution of methylacetoacetate (1.2 g, 8.5 mmol), 2-methoxy-6-(8'Z, 11'Z) pentadecadienyl benzaldehyde (3.1 g, 8.5 mmol) and urea (1.00 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography.

IR ($cm^{-1}$): 3426 (N—H), 2920 (C—H), 1690 (C═O)

Mass (Electrospray): 483 (M+1), 481 (M−1)

Example 16

5-methoxycarbonyl-4-(2-methoxy-6-(8'Z) pentadecenyl phenyl)-6-methyl-3,4-dihydropyrimidin-2(1H)-one (PPK-26C)

A solution of methylacetoacetate (1.2 g, 8.5 mmol), 2-methoxy-6-(8'Z) pentadecenyl benzaldehyde (3.1 g, 8.5 mmol) and urea (1.00 g, 17 mmol) in tetrahydrofuran (20 mL) was heated to reflux (65-70° C.) in the presence hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography.

IR ($cm^{-1}$): 3424 (N—H), 2924 (C—H), 1692 (C═O)

Mass (Electrospray): 485 (M+1), 483 (M−1)

Example 17

5-ethoxycarbonyl-4-(2-ethoxy-6-(8'Z,11'Z,14'Z) pentadecatrienyl phenyl)-6-methyl-3,4-dihydropyrimidin-2(1H)-one (PPK-27A)

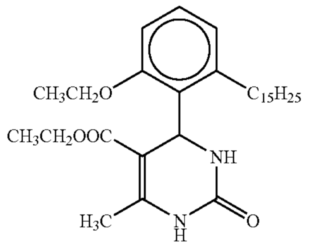

A solution of ethylacetoacetate (1.3 g, 8.5 mmol), 2-ethoxy-6-(8'Z,11'Z,14'Z) pentadecatrienyl benzaldehyde (3.2 g, 8.5 mmol) and urea (1.1 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography and recrystallised from hexane to get white crystalline solid of title compound.

IR ($cm^{-1}$): 3422 (N—H), 2920 (C—H), 1690 (C═O)

Mass (Electrospray): 509 (M+1), 507 (M−1)

Example 18

5-ethoxycarbonyl-4-(2-ethoxy-6-(8'Z, 11'Z) pentadecadienyl phenyl)-6-methyl-3,4-dihydropyrimidin-2(1H)-one (PPK-27B)

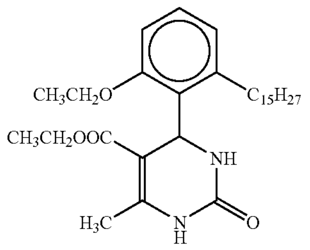

A solution of ethylacetoacetate (1.3 g, 8.5 mmol), 2-ethoxy-6-(8'Z,11'Z) pentadecadienyl benzaldehyde (3.2 g, 8.5 mmol) and urea (1.1 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography.

IR ($cm^{-1}$): 3424 (N—H), 2924 (C—H), 1691 (C═O)

Mass (Electrospray): 511 (M+1), 509 (M−1)

Example 19

5-ethoxycarbonyl-4-(2-ethoxy-6-(8'Z) pentadecenyl phenyl)-6-methyl-3,4-dihydropyrimidin-2(1H)-one (PPK-27C)

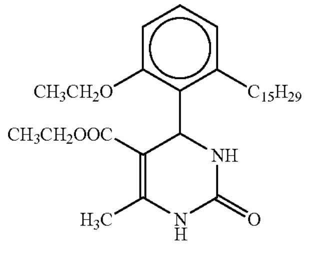

A solution of ethylacetoacetate (1.3 g, 8.5 mmol), 2-ethoxy-6-(8'Z) pentadecenyl benzaldehyde (3.2 g, 8.5 mmol) and urea (1.1 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography.

IR ($cm^{-1}$): 3423 (N—H), 2923 (C—H), 1691 (C═O)

Mass (Electrospray): 513 (M+1), 511 (M−1)

Example 20

5-methoxycarbonyl-4-(2-ethoxy-6-(8'Z, 11'Z, 14'Z) pentadecatrienyl phenyl)-6-methyl-3,4-dihydropyrimidin-2(1H)-one (PPK-28A)

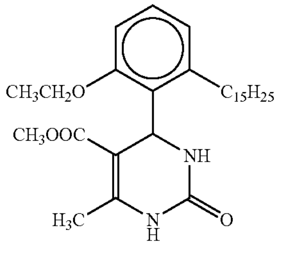

A solution of methylacetoacetate (1.2 g, 8.5 mmol), 2-ethoxy-6-(8'Z,11'Z,14'Z) pentadecatrienyl benzaldehyde (3.2 g, 8.5 mmol) and urea (1.1 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography and recrystallised from hexane to get white crystalline solid of title compound.

IR ($cm^{-1}$): 3421 (N—H), 2920 (C—H), 1690 (C═O)

Mass (Electrospray): 495 (M+1), 493 (M−1)

Example 21

5-methoxycarbonyl-4-(2-ethoxy-6-(8'Z,11'Z) pentadecadienyl phenyl)-6-methyl-3,4-dihydropyrimidin-2(1H)-one (PPK-28B)

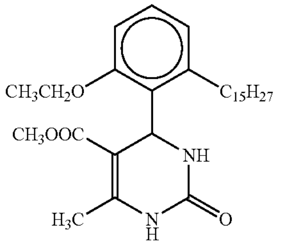

A solution of methylacetoacetate (1.2 g, 8.5 mmol), 2-ethoxy-6-(8'Z,11'Z) pentadecadienyl benzaldehyde (3.2 g, 8.5 mmol) and urea (1.1 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography.

IR ($cm^{-1}$): 3423 (N—H), 2921 (C—H), 1690 (C═O)

Mass (Electrospray): 497 (M+1), 495 (M−1)

Example 22

5-methoxycarbonyl-4-(2-ethoxy-6-(8'Z) pentadecenyl phenyl)-6-methyl-3,4-dihydropyrimidin-2(1H)-one (PPK-28C)

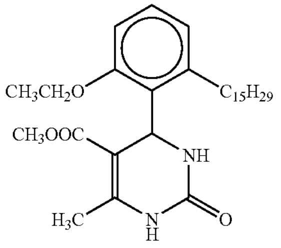

A solution of methylacetoacetate (1.2 g, 8.5 mmol), 2-ethoxy-6-(8'Z) pentadecenyl benzaldehyde (3.2 g, 8.5 mmol) and urea (1.1 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography.

IR ($cm^{-1}$): 3422 (N—H), 2921 (C—H), 1691 (C═O)

Mass (Electrospray): 499 (M+1), 497 (M−1)

Example 23

5-isopropoxycarbonyl-4-(2-ethoxy-6-(8'Z,11'Z,14'Z) pentadecatrienyl phenyl)-6-methyl-3,4-dihydropyrimidin-2(1H)-one (PPK-29A)

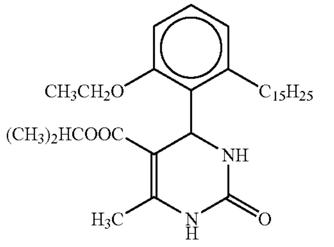

A solution of isopropylacetoacetate (1.3 g, 8.5 mmol), 2-ethoxy-6-(8'Z,11'Z,14'Z) pentadecatrienyl benzaldehyde (3.2 g, 8.5 mmol) and urea (1.1 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography and recrystallised from hexane to get white crystalline solid of title compound.

IR ($cm^{-1}$): 3421 (N—H), 2920 (C—H), 1690 (C═O)

Mass (Electrospray): 523 (M+1), 521 (M−1)

Example 24

5-isopropoxycarbonyl-4-(2-ethoxy-6-(8'Z,11'Z) pentadecadienyl phenyl)-6-methyl-3,4-dihydropyrimidin-2(1H)-one (PPK-29B)

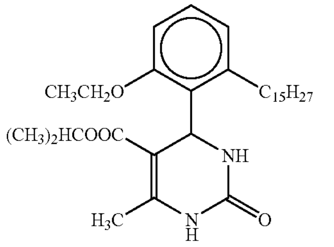

A solution of isopropylacetoacetate (1.3 g, 8.5 mmol), 2-ethoxy-6-(8'Z,11'Z) pentadecadienyl benzaldehyde (3.2 g, 8.5 mmol) and urea (1.1 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography.

IR ($cm^{-1}$): 3423 (N—H), 2921 (C—H), 1690 (C═O)

Mass (Electrospray): 525 (M+1), 523 (M−1)

Example 25

5-isopropoxycarbonyl-4-(2-ethoxy-6-(8'Z) pentadecenyl phenyl)-6-methyl-3,4-dihydropyrimidin-2(1H)-one (PPK-29C)

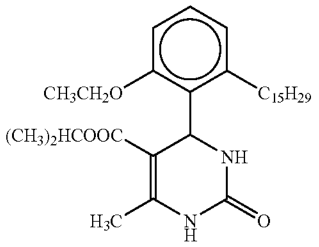

A solution of isopropylacetoacetate (1.3 g, 8.5 mmol), 2-ethoxy-6-(8' Z) pentadecenyl benzaldehyde (3.2 g, 8.5 mmol) and urea (1.1 g, 17 mmol) in tetrahydrofuran (20 mL) was heated to reflux (65-70° C.) in the presence of hydrochloric acid (30%) for 7 h. The reaction mixture after being cooled to room temperature was poured into crushed ice (20 g) and stirred for 5 min. The viscous liquid was extracted with ethylacetate (40 mL) and was washed with 1N hydrochloric acid, water, sodium bicarbonate and brine. After drying over anhydrous sodium sulfate, the solvent was evaporated to yield light yellow oil. This crude product was purified by flash column chromatography.

IR ($cm^{-1}$): 3422 (N—H), 2921 (C—H), 1691 (C═O)

Mass (Electrospray): 527 (M+1), 525 (M−1)

Example 26

3,6-dihydro-4-methyl-6-[2-methoxy-6-pentadecylphenyl]-2-oxo-1,5-(2H)-pyrimidinedicarboxylic acid 1-ethyl 5-methyl diester. (PPK-30)

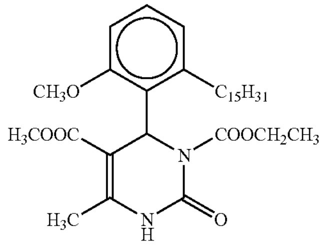

The solution of 1,4-dihydro-2-[[(4-methoxyphenyl)methyl)oxy]-6-methyl-4-[2-methoxy-6-pentadecylphenyl]-5-pyrimidinecarboxylic acid methyl ester (3 g, 4.6 mmol) in dichloromethane (15 mL) and pyridine (1.5 mL) was treated with ethyl chloroformate (0.6 g, 4.7 mmol) at 0° C. under argon. After the addition was finished reaction was stirred at room temperature for 12 h and then diluted with more dichloromethane. The resultant solution was washed with 1N hydrochloric acid, water, sodium bicarbonate and brine. After drying over anhydrous sodium sulfate, the solvent evaporated to yield light yellow oil. This crude product was purified by flash column chromatography and recrystallised from hexane to get white crystalline solid of title compound.

Melting point: 121-122° C.

IR ($cm^{-1}$): 3340 (N—H), 2921 (C—H), 1696 (C═O)

Mass (Electrospray): 559 (M+1), 557 (M−1)

$^1H$ NMR (δ ppm): 8.35 (bs, 1H, $D_2O$ exchangeable, N—H) 7.2 (t, J=8 Hz, 1H, aromatic proton) 6.85 (d, J=8 Hz, 1H, aromatic proton) 6.7 (d, J=8 Hz, 1H, aromatic proton) 6.55 (s, 1H, $C_6$—H) 4.25 (q, 2H, J=6 Hz, O—$CH_2$) 3.75 (s, 3H, O—$CH_3$) 3.6 (s, 3H, O—$CH_3$) 3.1 (m, 1H, benzylic) 3.0 (m, 1H, benzylic) 2.25 (s, 3H, allylic) 1.85-1.1 (m, 29H, $(CH_2)_{13}$ from alkyl chain, $CH_3$) 0.9 (dt, 3H, terminal $CH_3$ from alkyl chain).

bs-broad singlet, t-triplet, d-doublet, s-singlet, m-multiplet, dt-distorted triplet.

Example 27

3,6-dihydro-4-methyl-6-[2-methoxy-6-pentadecylphenyl]-2-oxo-1,5-(2H)-pyrimidinedicarboxylic acid bis(ethyl ester). (PPK-31)

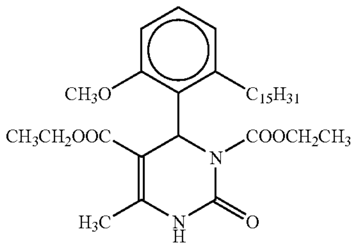

The solution of 1,4-dihydro-2-[[(4-methoxyphenyl)methyl)oxy]-6-methyl-4-[2-methoxy-6-pentadecylphenyl]-5-pyrimidinecarboxylic acid ethyl ester (3 g, 4.7 mmol) in dichloromethane (15 mL) and pyridine (1.5 mL) was treated with ethyl chloroformate (0.6 g, 4.7 mmol) at 0° C. under argon. After the addition was finished reaction was stirred at room temperature for 12 h and then diluted with more dichloromethane. The resultant solution was washed with 1N hydrochloric acid, water, sodium bicarbonate and brine. After drying over anhydrous sodium sulfate, the solvent evaporated to yield light yellow oil. This crude product was purified by flash column chromatography and recrystallised from hexane to get white crystalline solid of title compound.

Melting point: 109-110° C.

IR ($cm^{-1}$): 3348 (N—H), 2920 (C—H), 1697 (C═O)

Mass (Electrospray): 573 (M+1), 571 (M−1)

$^1H$ NMR (δ ppm): 8.1 (bs, 1H, $D_2O$ exchangeable, N—H) 7.15 (t, J=8 Hz, 1H, aromatic proton) 6.85 (d, J=8 Hz, 1H, aromatic proton) 6.7 (d, J=8 Hz, 1H, aromatic proton) 6.55 (s, 1H, $C_6$—H) 4.1 (m, 4H, O—$CH_2$) 3.75 (s, 3H, O—$CH_3$) 3.1 (m, 1H, benzylic) 2.9 (m, 1H, benzylic) 2.25 (s, 3H, allylic) 1.85-1.1 (m, 32H, $(CH_2)_{13}$ from alkyl chain, $CH_3$, $CH_3$) 0.9 (dt, 3H, terminal $CH_3$ from alkyl chain).

bs-broad singlet, t-triplet, d-doublet, s-singlet, m-multiplet, dt-distorted triplet.

Example 28

3,6-dihydro-4-methyl-6-[2-methoxy-6-pentadecylphenyl]-2-oxo-1,5-(2H)-pyrimidinedicarboxylic acid 1-ethyl 5-isopropyl diester (PPK-32)

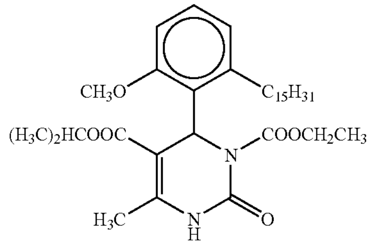

The solution of 1,4-dihydro-2-[[(4-methoxyphenyl)methyl)oxy]-6-methyl-4-[2-methoxy-6-pentadecylphenyl]-5-pyrimidinecarboxylic acid isopropyl ester (3 g, 4.8 mmol) in dichloromethane (15 mL) and pyridine (1.6 mL) was treated with ethyl chloroformate (0.7 g, 4.8 mmol) at 0° C. under argon. After the addition was finished reaction was stirred at room temperature for 12 h and then diluted with more dichloromethane. The resultant solution was washed with 1N hydrochloric acid, water, sodium bicarbonate and brine. After drying over anhydrous sodium sulfate, the solvent evaporated to yield light yellow oil. This crude product was purified by flash column chromatography and recrystallised from hexane to get white crystalline solid of title compound.

Melting point: 100° C.

IR ($cm^{-1}$): 3341 (N—H), 2919 (C—H), 1698 (C═O)

Mass (Electrospray): 587 (M+1), 585 (M−1)

$^1H$ NMR (δ ppm): 8.3 (bs, 1H, $D_2O$ exchangeable, N—H) 7.2 (t, J=8 Hz, 1H, aromatic proton) 6.85 (d, J=8 Hz, 1H, aromatic proton) 6.7 (d, J=8 Hz, 1H, aromatic proton) 6.57 (s, 1H, $C_6$—H) 5.0 (m, 1H, $OCH(CH_3)_2$) 4.25 (q, 2H, J=6 Hz, O—$CH_2$) 3.75 (s, 3H, O—$CH_3$) 3.2 (m, 1H, benzylic) 3.0 (m, 1H, benzylic) 2.25 (s, 3H, allylic) 1.9-1.0 (m, 35H, $(CH_2)_{13}$ from alkyl chain, $CH_3$, $(CH_3)_2$) 0.87 (dt, 3H, terminal $CH_3$ from alkyl chain).

bs-broad singlet, t-triplet, d-doublet, s-singlet, m-multiplet, dt-distorted triplet.

Example 29

3,6-dihydro-4-methyl-6-[2-ethoxy-6-pentadecylphenyl]-2-oxo-1,5-(2H)-pyrimidinedicarboxylic acid 1-ethyl 5-methyl diester. (PPK-33)

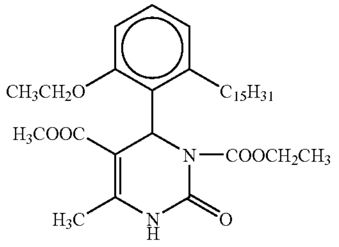

The solution of 1,4-dihydro-2-[[(4-methoxyphenyl)methyl)oxy]-6-methyl-4-[2-ethoxy-6-pentadecylphenyl]-5-pyrimidinecarboxylic acid methyl ester (3 g, 4.7 mmol) in dichloromethane (15 mL) and pyridine (1.5 mL) was treated with ethyl chloroformate (0.7 g, 4.8 mmol) at 0° C. under argon. After the addition was finished reaction was stirred at room temperature for 12 h and then diluted with more dichloromethane. The resultant solution was washed with 1N hydrochloric acid, water, sodium bicarbonate and brine. After drying over anhydrous sodium sulfate, the solvent was evaporated to yield light yellow oil. This crude product was purified by flash column chromatography and recrystallised from hexane to get white crystalline solid of title compound.

Melting point: 103° C.

IR ($cm^{-1}$): 3346 (N—H), 2918 (C—H), 1698 (C═O)

Mass (Electrospray): 573 (M+1), 571 (M−1)

$^1$H NMR (δ ppm): 7.4 (bs, 1H, N—H) 7.15 (t, J=7 Hz, 1H, aromatic proton) 6.85 (d, J=8 Hz, 1H, aromatic proton) 6.7 (d, J=8 Hz, 1H, aromatic proton) 6.6 (s, 1H, $C_6$—H) 4.2 (m, 2H, O—$CH_2$) 4.0 (q, 2H, J=6 Hz, O—$CH_2$) 3.6 (s, 3H, O—$CH_3$) 3.15 (m, 1H, benzylic) 2.95 (m, 1H, benzylic) 2.28 (s, 3H, allylic) 1.85-1.0 (m, 32H, $(CH_2)_{13}$ from alkyl chain, $CH_3$, $CH_3$) 0.9 (dt, 3H, terminal $CH_3$ from alkyl chain).

bs-broad singlet, t-triplet, d-doublet, s-singlet, m-multiplet, dt-distorted triplet, q-quartet.

Example 30

3,6-dihydro-4-methyl-6-[2-ethoxy-6-pentadecylphenyl]-2-oxo-1,5-(2H)-pyrimidinedicarboxylic acid 1,5-diethyl diester. (PPK-34)

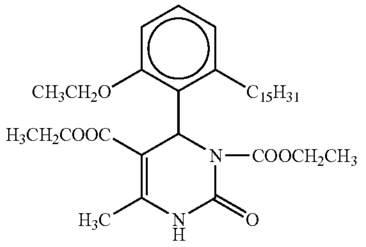

The solution of 1,4-dihydro-2-[[(4-methoxyphenyl)methyl)oxy]-6-methyl-4-[2-ethoxy-6-pentadecylphenyl]-5-pyrimidinecarboxylic acid ethyl ester (3 g, 4.65 mmol) in dichloromethane (15 mL) and pyridine (1.5 mL) was treated with ethyl chloroformate (0.7 g, 4.7 mmol) at 0° C. under argon. After the addition was finished reaction was stirred at room temperature for 12 h and then diluted with more dichloromethane. The resultant solution was washed with 1N hydrochloric acid, water, sodium bicarbonate and brine. After drying over anhydrous sodium sulfate, the solvent was evaporated to yield light yellow oil. This crude product was purified by flash column chromatography and recrystallised from hexane to get white crystalline solid of title compound.

Melting point: 112° C.

IR ($cm^{-1}$): 3342 (N—H), 2920 (C—H), 1697 (C═O)

Mass (Electrospray): 587 (M+1), 585 (M−1)

$^1$H NMR (δ ppm): 7.25 (bs, 1H, N—H) 7.15 (t, J=7 Hz, 1H, aromatic proton) 6.85 (d, J=8 Hz, 1H, aromatic proton) 6.7 (d, J=8 Hz, 1H, aromatic proton) 6.6 (s, 1H, $C_6$—H) 4.2 (m, 6H, O—$CH_2$) 3.2 (m, 1H, benzylic) 2.95 (m, 1H, benzylic) 2.3 (s, 3H, allylic) 1.85-1.15 (m, 32H, $(CH_2)_{13}$ from alkyl chain, $CH_3$, $CH_3$, $CH_3$) 0.9 (dt, 3H, terminal $CH_3$ from alkyl chain).

bs-broad singlet, t-triplet, d-doublet, s-singlet, m-multiplet, dt-distorted triplet, q-quartet.

Example 31

3,6-dihydro-4-methyl-6-[2-ethoxy-6-pentadecylphenyl]-2-oxo-1,5-(2H)-pyrimidinedicarboxylic acid 1-ethyl 5-isopropyl diester (PPK-35)

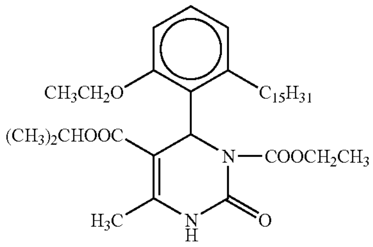

The solution of 1,4-dihydro-2-[[(4-methoxyphenyl)methyl)oxy]-6-methyl-4-[2-ethoxy-6-pentadecylphenyl]-5-pyrimidinecarboxylic acid isopropyl ester (3 g, 4.8 mmol) in dichloromethane (15 mL) and pyridine (1.5 mL) was treated with ethyl chloroformate (0.7 g, 4.8 mmol) at 0° C. under argon. After the addition was finished reaction was stirred at room temperature for 12 h and then diluted with more dichloromethane. The resultant solution was washed with 1N hydrochloric acid, water, sodium bicarbonate and brine. After drying over anhydrous sodium sulfate, the solvent was evaporated to yield light yellow oil. This crude product was purified by flash column chromatography and recrystallised from hexane to get white crystalline solid of title compound.

Melting point: 110-111° C.

IR ($cm^{-1}$): 3350 (N—H), 2920 (C—H), 1696 (C═O)

Mass (Electrospray): 601 (M+1), 599 (M−1)

$^1$H NMR (δ ppm): 7.15 (m, 2H, $D_2O$ exchangeable for 1H, N—H, aromatic proton) 6.8 (d, J=8 Hz, 1H, aromatic proton) 6.6 (d, J=8 Hz, 1H, aromatic proton) 6.5 (s, 1H, $C_6$—H) 5.0 (m, 1H, $OCH(CH_3)_3$) 4.25 (m, 2H, $CH_2$) 4.0 (q, 2H, O—$CH_2$) 3.25 (m, 1H, benzylic) 3.0 (m, 1H, benzylic) 2.3 (s, 3H, allylic) 1.85-1.0 (m, 38H, $(CH_2)_{13}$ from alkyl chain, $(CH_3)_2$, $CH_3$, $CH_3$) 0.9 (dt, 3H, terminal $CH_3$ from alkyl chain).

bs-broad singlet, t-triplet, d-doublet, s-singlet, m-multiplet, dt-distorted triplet, q-quartet.

Example 32

3,6-dihydro-4-methyl-6-[2-isopropoxy-6-pentadecylphenyl]-2-oxo-1,5-(2H)-pyrimidinedicarboxylic acid 1-ethyl 5-methyl diester (PPK-36)

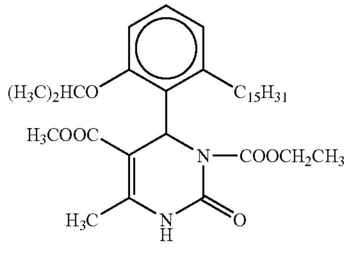

The solution of 1,4-dihydro-2-[[(4-methoxyphenyl)methyl)oxy]-6-methyl-4-[2-isopropoxy-6-pentadecylphenyl]-5-pyrimidinecarboxylic acid methyl ester (3 g, 4.7 mmol) in dichloromethane (15 mL) and pyridine (1.5 mL) was treated with ethyl chloroformate (0.7 g, 4.8 mmol) at 0° C. under argon. After the addition was finished reaction was stirred at room temperature for 12 h and then diluted with more dichloromethane. The resultant solution was washed with 1N hydrochloric acid, water, sodium bicarbonate and brine. After drying over anhydrous sodium sulfate, the solvent was evaporated to yield light yellow oil. This crude product was purified by flash column chromatography and recrystallised from hexane to get white crystalline solid of title compound.

Melting point: 120-121° C.

IR ($cm^{-1}$): 3342 (N—H), 2921 (C—H), 1670 (C═O)

Mass (Electrospray): 587 (M+1), 585 (M−1)

$^1$H NMR (δ ppm): 7.85 (bs, 1H, N—H) 7.15 (t, J=7 Hz, 1H, aromatic proton) 6.8 (d, J=8 Hz, 1H, aromatic proton) 6.7 (d, J=8 Hz, 1H, aromatic proton) 6.55 (s, 1H, $C_6$—H) 4.65 (m, 1H, $OCH(CH_3)_2$) 4.2 (q, 2H, J=6 Hz, O—$CH_2$) 3.6 (s, 3H, O—$CH_3$) 3.0 (m, 2H, benzylic) 2.28 (s, 3H, allylic) 1.95-1.0 (m, 35H, $(CH_2)_{13}$ from alkyl chain, $(CH_3)_2$, $CH_3$) 0.85 (dt, 3H, terminal $CH_3$ from alkyl chain).

bs-broad singlet, t-triplet, d-doublet, s-singlet, m-multiplet, dt-distorted triplet, q-quartet.

Example 33

3,6-dihydro-4-methyl-6-[2-isopropoxy-6-pentadecylphenyl]-2-oxo-1,5-(2H)-pyrimidinedicarboxylic acid 1,5-diethyl diester. (PPK-37)

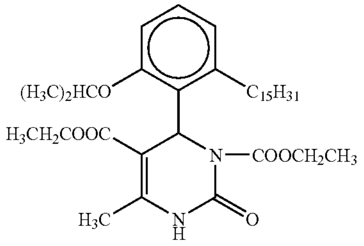

The solution of 1,4-dihydro-2-[[(4-methoxyphenyl)methyl)oxy]-6-methyl-4-[2-ethoxy-6-pentadecylphenyl]-5-pyrimidinecarboxylic acid ethyl ester (3 g, 4.6 mmol) in dichloromethane (15 mL) and pyridine (1.5 mL) was treated with ethyl chloroformate (0.8 g, 4.7 mmol) at 0° C. under argon. After the addition was finished reaction was stirred at room temperature for 12 h and then diluted with more dichloromethane. The resultant solution was washed with 1N hydrochloric acid, water, sodium bicarbonate and brine. After drying over anhydrous sodium sulfate, the solvent was evaporated to yield light yellow oil. This crude product was purified by flash column chromatography and recrystallised from hexane to get white crystalline solid of title compound.

Melting point: 90-92° C.

IR ($cm^{-1}$): 3340 (N—H), 2920 (C—H), 1696 (C═O)

Mass (Electrospray): 601 (M+1), 599 (M−1)

$^1$H NMR (δ ppm): 7.6 (bs, 1H, N—H) 7.15 (dt, 1H, aromatic proton) 6.8 (d, J=8 Hz, 1H, aromatic proton) 6.7 (d, J=8 Hz, 1H, aromatic proton) 6.55 (s, 1H, $C_6$—H) 4.65 (m, 1H, $OHC(CH_3)_2$) 4.1 (m, 4H, O—$CH_2$) 3.15 (m, 1H, benzylic) 2.95 (m, 1H, benzylic) 2.2 (s, 3H, allylic) 1.9-1.0 (m, 38H, $(CH_2)_{13}$ from alkyl chain, $CH_3$, $CH_3$, $(CH_3)_2$) 0.9 (dt, 3H, terminal $CH_3$ from alkyl chain).

bs-broad singlet, t-triplet, d-doublet, s-singlet, m-multiplet, dt-distorted triplet, q-quartet.

Example 34

3,6-dihydro-4-methyl-6-[2-isopropoxy-6-pentadecylphenyl]-2-oxo-1,5-(2H)-pyrimidinedicarboxylic acid 1-ethyl 5-isopropyl diester. (PPK-38)

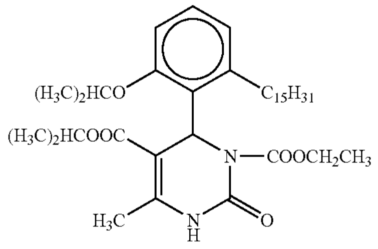

The solution of 1,4-dihydro-2-[[(4-methoxyphenyl)methyl)oxy]-6-methyl-4-[2-ethoxy-6-pentadecylphenyl]-5-pyrimidinecarboxylic acid isopropyl ester (3 g, 4.5 mmol) in dichloromethane (15 mL) and pyridine (1.5 mL) was treated with ethyl chloroformate (0.85 g, 4.6 mmol) at 0° C. under argon. After the addition was finished reaction was stirred at room temperature for 12 h and then diluted with more dichloromethane. The resultant solution was washed with 1N hydrochloric acid, water, sodium bicarbonate and brine. After drying over anhydrous sodium sulfate, the solvent was evaporated to yield light yellow oil. This crude product was purified by flash column chromatography and recrystallised from hexane to get white crystalline solid of title compound.

Melting point 88-90° C.

IR ($cm^{-1}$): 3340 (N—H), 2918 (C—H), 1695 (C═O)

Mass (Electrospray): 615 (M+1), 613 (M−1)

$^1$H NMR (δ ppm): 7.7 (bs, 1H, N—H) 7.17 (dt, 1H, aromatic proton) 6.8 (d, J=8 Hz, 1H, aromatic proton) 6.7 (d, J=8 Hz, 1H, aromatic proton) 6.5 (s, 1H, $C_6$—H) 5.0 (m, 1H, $OHC(CH_3)_2$) 4.7 (m, 1H, $OHC(CH_3)_2$) 4.23 (q, J=6 Hz, 2H, O—$CH_2$) 3.2 (m, 1H, benzylic) 3.0 (m, 1H, benzylic) 2.25 (s, 3H, allylic) 1.9-1.0 (m, 41H, $(CH_2)_{13}$ from alkyl chain, $CH_3$, $(CH_3)_2$, $(CH_3)_2$) 0.9 (dt, 3H, terminal $CH_3$ from alkyl chain).

bs-broad singlet, t-triplet, d-doublet, s-singlet, m-multiplet, dt-distorted triplet, q-quartet.

Example 35

3,6-dihydro-4-(2'-mercapto-1'H-benzimidazolyl)methyl-6-[2-methoxy-6-pentadecylphenyl]-2-oxo-1,5-(2H)-pyrimidinedicarboxylic acid bis(ethyl ester)

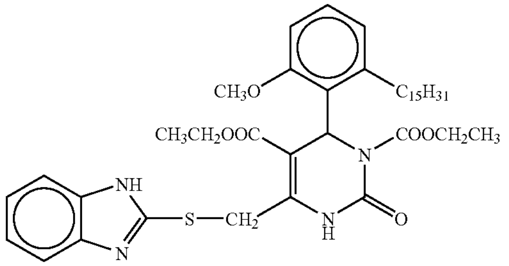

The solution of 1,4-dihydro-2-[[(4-methoxyphenyl)methyl)oxy]-6-(2'-mercapto-1'H-benzimidazolyl)methyl-4-[2-methoxy-6-pentadecylphenyl]-5-pyrimidinecarboxylic acid ethyl ester (3 g, 4.9 mmol) in dichloromethane (15 mL) and pyridine (2.0 mL) was treated with ethyl chloroformate (0.7 g, 4.9 mmol) at 0° C. under argon. After the addition was finished reaction was stirred at room temperature for 12 h and then diluted with more dichloromethane. The resultant solution was washed with 1N hydrochloric acid, water, sodium bicarbonate and brine. After drying over anhydrous sodium sulfate, the solvent was evaporated to yield light yellow oil. This crude product was purified by flash column chromatography to obtain the title compound.

IR ($cm^{-1}$): 3450 (N—H), 2921 (C—H), 1686 (C=O)

Mass (Electrospray): 721 (M+1), 719 (M−1)

$^1$H NMR (δ ppm): 8.5 (bs, 1H, $D_2O$ exchangeable, N—H) 7.7 (d, J=6 Hz, 1H, Aromatic proton) 7.5 (m, 1H, Aromatic proton) 7.25 (m, 2H, Aromatic proton) 7.15 (t, J=8 Hz, 1H, Aromatic proton) 6.85 (d, J=8 Hz, 2H, Aromatic proton) 5.8 (s, 1H, $C_6$—H) 4.6 (s, 1H, $D_2O$ exchangeable, N—H) 4.5 (s, 2H, S—$CH_2$) 4.0 (m, J=6 Hz, 4H, O—$CH_2$) 3.7 (s, 3H, O—$CH_3$) 3.1 (m, 1H, benzylic) 2.5 (m, 1H, benzylic) 1.85-1.1 (m, 35H, $(CH_2)_{13}$ from alkyl chain, $CH_3$, $CH_3$, allylic $CH_3$) 0.9 (dt, 3H, terminal $CH_3$ from alkyl chain).

bs-broad singlet, t-triplet, d-doublet, s-singlet, m-multiplet, dt-distorted triplet.

Example 36

3,6-dihydro-4-methyl-6-[2-isopropoxy-6-pentadecylphenyl]-2-oxo-1,5-(2H)-pyrimidinedicarboxylic acid 1,5-bis(methyl ester)

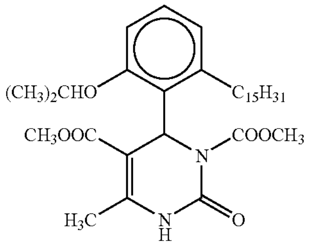

The solution of 1,4-dihydro-2-[[(4-methoxyphenyl)methyl)oxy]-6-methyl-4-[2-isopropoxy-6-pentadecylphenyl]-5-pyrimidinecarboxylic acid methyl ester (3 g, 4.8 mmol) in dichloromethane (15 mL) and pyridine (1.5 mL) was treated with ethyl chloroformate (0.7 g, 4.8 mmol) at 0° C. under argon. After the addition was finished reaction was stirred at room temperature for 12 h and then diluted with more dichloromethane. The resultant solution was washed with 1N hydrochloric acid, water, sodium bicarbonate and brine. After drying over anhydrous sodium sulfate, the solvent was evaporated to yield light yellow oil. This crude product was purified by flash column chromatography to obtain the title compound.

IR ($cm^{-1}$): 3352 (N—H), 2921 (C—H), 1692 (C=O)

Mass (Electrospray): 573 (M+1), 571 (M−1)

$^1$H NMR (δ ppm): 8.0 (bs, 1H, $D_2O$ exchangeable, N—H) 7.1 (t, J=8 Hz, 1H, aromatic proton) 6.95 (d, J=8 Hz, 1H, aromatic proton) 6.8 (d, J=8 Hz, 1H, aromatic proton) 6.65 (s, 1H, $C_6$—H) 4.0 (s, 3H, $COOCH_3$) 3.75 (s, 3H, N—$COOCH_3$) 3.0 (m, 1H, benzylic) 2.85 (m, 1H, benzylic) 2.2 (s, 3H, allylic) 1.85-1.1 (m, 32H, $(CH_2)_{13}$ from alkyl chain, $(CH_3)_2$) 0.9 (dt, 3H, terminal $CH_3$ from alkyl chain).

bs-broad singlet, t-triplet, d-doublet, s-singlet, m-multiplet, dt-distorted triplet.

Example 37

3,6-dihydro-4-methyl-6-[2-methoxy-6-pentadecylphenyl]-2-thioxo-1,5-(2H)-pyrimidinedicarboxylic acid bis(ethyl ester)

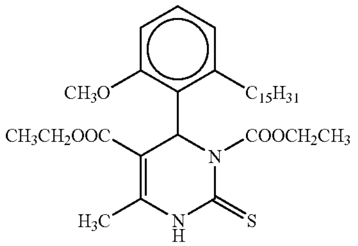

The solution of 1,4-dihydro-2-[[(4-methoxyphenyl)methyl)thio]-6-methyl-4-[2-methoxy-6-pentadecylphenyl]-5-pyrimidinecarboxylic acid ethyl ester (3 g, 4.7 mmol) in dichloromethane (15 mL) and pyridine (1.5 mL) was treated with ethyl chloroformate (0.6 g, 4.7 mmol) at 0° C. under argon. After the addition was finished reaction was stirred at room temperature for 2 h and then diluted with more dichloromethane. The resultant solution was washed with 1N hydrochloric acid, water, sodium bicarbonate and brine. After drying over anhydrous sodium sulfate, the solvent evaporated to yield light yellow oil. This was dissolved in dichloromethane (20 mL) and treated with trifloro acetic acid (2.0 mL) and ethanethiol (1.0 mL). The reaction was stirred at room temperature overnight, and the solvent was evaporated and the crude product was purified by flash column chromatography to obtain the title compound.

IR ($cm^{-1}$): 3350 (N—H), 2921 (C—H), 1696 (C=O)

Mass (Electrospray): 589 (M+1), 587 (M−1)

$^1$H NMR (δ ppm): 7.6 (bs, 1H, $D_2O$ exchangeable, N—H) 7.1 (t, J=8 Hz, 1H, aromatic proton) 6.8 (d, J=8 Hz, 1H, aromatic proton) 6.65 (d, J=8 Hz, 1H, aromatic proton) 6.5 (s, 1H, $C_6$—H) 4.05 (m, 4H, O—$CH_2$) 3.7 (s, 3H, O—$CH_3$) 3.05 (m, 1H, benzylic) 2.95 (m, 1H, benzylic) 2.2 (s, 3H, allylic) 1.85-1.1 (m, 32H, $(CH_2)_{13}$ from alkyl chain, $CH_3$, $CH_3$) 0.9 (dt, 3H, terminal $CH_3$ from alkyl chain).

bs-broad singlet, t-triplet, d-doublet, s-singlet, m-multiplet, dt-distorted triplet

CONCLUSION

Thus, those of skill in the art will appreciate that the compounds and uses disclosed herein can be used as calcium channel blockers, providing a therapeutic effect.

One skilled in the art will appreciate that these methods and compounds are and may be adapted to carry out the objects and obtain the ends and advantages mentioned, as well as those inherent therein. The methods, procedures, and compounds described herein are presently representative of preferred embodiments and are exemplary and are not intended as limitations on the scope of the invention. Changes therein and other uses will occur to those skilled in the art which are encompassed within the spirit of the invention and are defined by the scope of the claims.

It will be apparent to one skilled in the art that varying substitutions and modifications may be made to the invention disclosed herein without departing from the scope and spirit of the invention.

Those skilled in the art recognize that the aspects and embodiments of the invention set forth herein may be practiced separate from each other or in conjunction with each other. Therefore, combinations of separate embodiments are within the scope of the invention as claimed herein.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

What is claimed is:

1. A compound of Formula I (I)

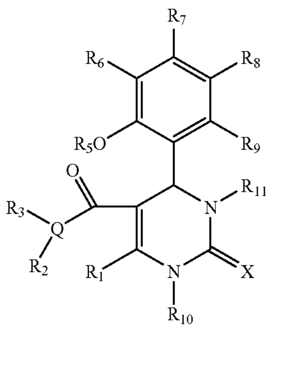

or a pharmaceutically acceptable salt thereof, wherein a) $R_1$-$R_3$ and $R_5$-$R_8$, are each independently selected from the group consisting of hydrogen, halogen, perhaloalkyl, nitro, amino, a diazo salt, lower alkyl, alkoxy, and optionally substituted five-membered or optionally substituted six-membered heteroaryl ring or optionally substituted six-membered aryl ring, wherein each said lower alkyl is independently and optionally substituted with one or more substituents selected from the group consisting of halogen, perhaloalkyl, nitro, amino, hydroxy, alkoxy, sulfhydryl, thioether, cyano, amido, ester, and

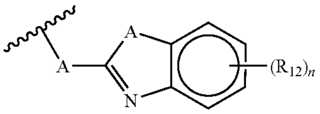

A is selected from the group consisting of oxygen, sulfur, sulfoxide, sulfone, and —NH;

$R_{12}$ is selected from the group consisting of hydrogen, hydroxy, alkoxy, haloalkoxy, halogen, haloalkyl, perhaloalkyl, nitro, amino, and a diazo salt; n is between 0-4; and said ring moieties are each independently and optionally substituted with a lower alkyl group, b) $R_9$ is selected from the group consisting of alkyl having at least 10 carbon atoms and a six-membered aryl ring, optionally substituted with one or more substituents selected from the group consisting of lower alkyl, halogen, perhaloalkyl, nitro, amino, cyano, amido, and ester; and c) $R_{10}$ is selected from the group consisting of hydrogen and lower alkyl d) $R_{11}$ is selected from the group consisting of:

i) hydrogen, alkyl, alkoxy, and a five-membered or six-membered heteroaryl ring or a six-membered aryl or heteroaryl ring, optionally substituted with one or more substituents selected from the group consisting of lower alkyl, halogen, perhaloalkyl, nitro, amino, cyano, amido, and ester;

ii) COY wherein Y is $C_1$-$C_8$ alkyl, $C_1$-$C_8$ alkoxy or $NR_{13}R_{14}$, wherein $R_{13}$ is hydrogen or $C_1$-$C_8$ alkyl and $R_{14}$ is hydrogen, $C_1$-$C_8$ alkyl, or $C_1$-$C_{14}$ phenalkyl;

iii) X or COX wherein X is

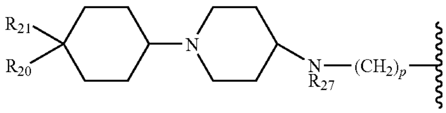

, iv) halogen, $CF_3$, cyano, nitro, $COONHR_{25}$, $COON(R_{25})_2$, $COOSO_2R_{28}$, $COONR_{25}SO_2N(R_{25})_2$, $CO_2R_{25}$, $COON(R_{25})_2$, $COOSO_2N(R_{25})_2$, $COOSO_2R_{28}$;

v) $CONR_{15}R_{16}$, wherein $R_{15}$ is selected from the group consisting of hydrogen, alkyl, cycloalkyl, aryl, or arylalkyl and $R_{16}$ is selected from the group consisting of hydrogen, alkyl, cycloalkyl, aryl, or halosubstituted alkyl, or $R_{15}$ and $R_{16}$ taken together with the nitrogen atom to which they are attached form 1-pyrrolidinyl, 1-piperidinyl, 1-azepinyl, 4-morpholinyl, 4-thiamorpholinyl, 1-piperazinyl, 4-diarylalkyl-1-piperazinyl, each of which is optionally substituted with one or more substituents selected from the group consisting of alkyl, alkoxy, alkylthio, halo, trifloromethyl, or hydroxy;

vi) Z, COOZ, or C(O)(NH)Z, wherein Z is selected from the group consisting of

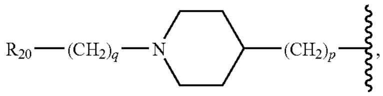,

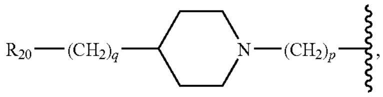,

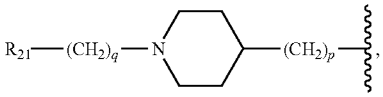, and

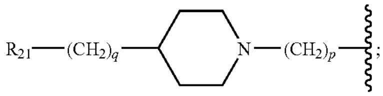;

wherein

A) p and q are each independently 0-10;

B) $R_{20}$ is phenyl optionally substituted with one or more substituents independently selected from the group consisting of halogen, $CF_3$, cyano, nitro, $N(R_{25})_2$, $NR_{25}CONR_{27}$, $NR_{25}CON(R_{27})_2$, $NR_{25}SO_2R_{28}$, $NR_{25}SO_2N(R_{27})_2$, $(CH_2)_{0-4}CO_2R_{25}$, $(CH_2)_{0-4}CON(R_{25})_2$, $(CH_2)_{0-4}SO_2N(R_{25})_2$, $(CH_2)_{0-4}SO_2R_{28}$, and $C_{1-4}$ alkyl;

C) $R_{21}$ is selected from the group consisting of hydrogen, cyano, $OR_{28}$, $COOR_{25}$, $CON(R_{25})_2$, and phenyl optionally substituted with one or more substituents independently selected from the group consisting of halogen, $CF_3$, cyano, nitro, $N(R_{25})_2$, $NR_{25}CONR_{27}$, $NR_{25}CON(R_{27})_2$, $NR_{25}SO_2R_{28}$, $NR_{25}SO_2N(R_{27})_2$, $(CH_2)_{0-4}CO_2R_{25}$, $(CH_2)_{0-4}CON(R_{25})_2$, $(CH_2)_{0-4}SO_2N(R_{25})_2$, $(CH_2)_{0-4}SO_2R_{28}$, and $C_{1-4}$ alkyl;

D) $R_{25}$ and $R_{27}$ are each independently selected from hydrogen, $C_{1-8}$ alkyl, $C_{3-8}$ cycloalkyl, $(CH_2)_{0-4}CF_3$; and E) $R_{28}$ is selected from the group consisting of hydrogen, $C_{1-8}$ alkyl, $C_{3-8}$ cycloalkyl, and $(CH_2)_{0-4}CF_3$;

e) X is oxygen or sulfur; and f) Q is oxygen or nitrogen; provided that when Q is oxygen $R_3$ does not exist.

2. The compound of claim 1, wherein $R_1$ is hydrogen or optionally substituted lower alkyl.

3. The compound of claim 1, wherein $R_1$ is optionally substituted lower alkyl.

4. The compound of claim 1, wherein $R_1$ is selected from the group consisting of methyl, ethyl, n-propyl, isopropyl, n-butyl, sec-butyl, tert-butyl, pentyl, and

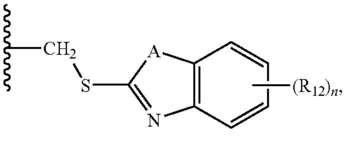, where A is selected from the group consisting of oxygen, sulfur, and —NH and $R_{12}$ is selected from the group consisting of hydrogen, hydroxy, alkoxy, haloalkoxy, halogen, haloalkyl, perhaloalkyl, nitro, amino, and a diazo salt, and n is between 0-4.

5. The compound of claim 1, wherein $R_2$ and $R_3$ are each independently selected from the group consisting of hydrogen, methyl, ethyl, n-propyl, isopropyl, n-butyl, sec-butyl, tert-butyl, and pentyl.

6. The compound of claim 1, wherein $R_5$ is selected from the group consisting of hydrogen, methyl, ethyl, n-propyl, isopropyl, n-butyl, sec-butyl, tert-butyl, and pentyl.

7. The compound of claim 1, wherein $R_6$—$R_8$ are each independently selected from the group consisting of hydrogen, methyl, ethyl, n-propyl, isopropyl, n-butyl, sec-butyl, tert-butyl, and pentyl.

8. The compound of claim 1, wherein $R_9$ alkyl having at least 10 carbon atoms.

9. The compound of claim 1, wherein $R_9$ is pentadecyl.

10. The compound of claim 1, wherein $R_{11}$ is selected from the group consisting of hydrogen, methoxy, ethoxy, and propoxy.

11. The compound of claim 1, wherein $R_{11}$ is COY wherein Y is $C_1$-$C_8$ alkyloxy or $NR_{13}R_{14}$, wherein $R_{13}$ is hydrogen or $C_1$-$C_8$ alkyl and $R_{14}$ is hydrogen, $C_1$-$C_8$ alkyl, or $C_1$-$C_{14}$ phenalkyl.

12. The compound of claim 11, wherein Y is ethoxy.

13. The compound of claim 11, wherein $R_{13}$ and $R_{14}$ are each methyl.

14. The compound of claim 1, wherein $R_{11}$ is X or COX.

15. The compound of claim 14, wherein p is 0 or 2.

16. The compound of claim 1, wherein $R_{11}$ is selected from the group consisting of, $COONHR_{25}$, $COON(R_{25})_2$, $COOSO_2R_{28}$, $COONR_{25}SO_2N(R_{25})_2$, $CO_2R_{25}$, $COON(R_{25})_2$, $COOSO_2N(R_{25})_2$, and $COOSO_2R_{28}$.

17. The compound of claim 1, wherein $R_{11}$ is Z, COOZ, or C(O)(NH)Z.

18. The compound of claim 17, wherein p and q are each independently 0 or 2.

19. The compound of claim 1, wherein $R_{20}$ is phenyl optionally substituted with one or more substituents independently selected from the group consisting of halogen, $CF_3$, cyano, nitro, $N(R_{25})_2$, $NR_{25}CONR_{27}$, $NR_{25}CON(R_{27})_2$, $NR_{25}SO_2R_{28}$, $NR_{25}SO_2N(_{27})_2$, $(CH_2)_{0-4}CO_2R_{25}$, $(CH_2)_{0-4}CON(R_{25})_2$, $(CH_2)_{0-4}SO_2N(R_{25})_2$, $(CH_2)_{0-4}SO_2R_{28}$, and $C_{1-4}$ alkyl.

20. The compound of claim 19, wherein said halogen is fluorine.

21. The compound of claim 19, wherein said phenyl is substituted with —$COOCH_3$.

22. The compound of claim 1, wherein the moiety —C(O)$QR_2R_3$ is —$C(O)NH_2$.

23. The compound of claim 1, wherein Q is oxygen and $R_3$ does not exist.

24. A compound selected from the group consisting of 5-ethoxycarbonyl-4-(2-ethoxy-6-pentadecylphenyl)-6-(2'-mercapto-1'H-benzimidazolyl)methyl-3,4-dihydropyrimidin-2(1H)-one;

5-ethoxycarbonyl-4-(2-methoxy-6-pentadecylphenyl)-6-methyl-3,4-dihydropyrimidin-2(1H)-one;

5-methoxycarbonyl-4-(2-ethoxy-6-pentadecylphenyl)-6-methyl-3,4-dihydropyrimidin-2(1H)-one;

5-methoxycarbonyl-4-(2-methoxy-6-pentadecylphenyl)-6-methyl-3,4-dihydropyrimidin-2(1H)-one;

5-ethoxycarbonyl-4-(2-ethoxy-6-pentadecylphenyl)-6-methyl-3,4-dihydropyrimidin-2(1H)-one;

5-methoxycarbonyl-4-(2-methoxy-6-(8'Z, 11'Z, 14'Z) pentadecatrienyl phenyl)-6-methyl-3,4-dihydropyrimidin-2(1H)-one;

5-methoxycarbonyl-4-(2-methoxy-6-(8'Z, 11'Z) pentadecadienyl phenyl)-6-methyl-3,4-dihydropyrimidin-2(1H)-one;

5-methoxycarbonyl-4-(2-methoxy-6-(8'Z) pentadecenyl phenyl)-6-methyl-3,4-dihydropyrimidin-2(1H)-one;

5-ethoxycarbonyl-4-(2-ethoxy-6-(8'Z, 11'Z, 14'Z) pentadecatrienyl phenyl)-6-methyl-3,4-dihydropyrimidin-2(1H)-one;

5-ethoxycarbonyl-4-(2-ethoxy-6-(8'Z, 11'Z) pentadecadienyl phenyl)-6-methyl-3,4-dihydropyrimidin-2(1H)-one;

5-ethoxycarbonyl-4-(2-ethoxy-6-(8'Z) pentadecenyl phenyl)-6-methyl-3,4-dihydropyrimidin-2(1H)-one;

5-methoxycarbonyl-4-(2-ethoxy-6-(8'Z, 11'Z, 14'Z) pentadecatrienyl phenyl)-6-methyl-3,4-dihydropyrimidin-2(1H)-one;

5-methoxycarbonyl-4-(2-ethoxy-6-(8'Z, 11'Z) pentadecadienyl phenyl)-6-methyl-3,4-dihydropyrimidin-2(1H)-one;

5-methoxycarbonyl-4-(2-ethoxy-6-(8'Z) pentadecenyl phenyl)-6-methyl-3,4-dihydropyrimidin-2(1H)-one;

5-isopropoxycarbonyl-4-(2-ethoxy-6-(8'Z, 11'Z, 14'Z) pentadecatrienyl phenyl)-6-methyl-3,4-dihydropyrimidin-2(1H)-one;

5-isopropoxycarbonyl-4-(2-ethoxy-6-(8'Z, 11'Z) pentadecadienyl phenyl)-6-methyl-3,4-dihydropyrimidin-2(1H)-one;

5-isopropoxycarbonyl-4-(2-ethoxy-6-(8'Z) pentadecenyl phenyl)-6-methyl-3,4-dihydropyrimidin-2(1H)-one;

3,6-dihydro-4-methyl-6-[2-methoxy-6-pentadecylphenyl]-2-oxo-1,5-(2H)-pyrimidinedicarboxylic acid 1-ethyl 5-methyl diester;

3,6-dihydro-4-methyl-6-[2-methoxy-6-pentadecylphenyl]-2-oxo-1,5-(2H)-pyrimidinedicarboxylic acid bis (ethyl ester);

3,6-dihydro-4-methyl-6-[2-methoxy-6-pentadecylphenyl]-2-oxo-1,5-(2H)-pyrimidinedicarboxylic acid 1-ethyl 5-isopropyl diester;

3,6-dihydro-4-methyl-6-[2-ethoxy-6-pentadecylphenyl]-2-oxo-1,5-(2H)-pyrimidinedicarboxylic acid 1-ethyl 5-methyl diester;

3,6-dihydro-4-methyl-6-[2-ethoxy-6-pentadecylphenyl]-2-oxo-1,5-(2H)-pyrimidinedicarboxylic acid 1,5-diethyl diester;

3,6-dihydro-4-methyl-6-[2-ethoxy-6-pentadecylphenyl]-2-oxo-1,5-(2H)-pyrimidinedicarboxylic acid 1-ethyl 5-isopropyl diester;

3,6-dihydro-4-methyl-6-[2-isopropoxy-6-pentadecylphenyl]-2-oxo-1,5-(2H)-pyrimidinedicarboxylic acid 1-ethyl 5-methyl diester;

3,6-dihydro-4-methyl-6-[2-isopropoxy-6-pentadecylphenyl]-2-oxo-1,5-(2H)-pyrimidinedicarboxylic acid 1,5-diethyl diester;

3,6-dihydro-4-methyl-6-[2-isopropoxy-6-pentadecylphenyl]-2-oxo-1,5-(2H)-pyrimidinedicarboxylic acid 1-ethyl, 5-isopropyl diester;

3,6-dihydro-4-methyl-6-(2-methoxy-6-pentadecylphenyl)-2-thioxo-1,5(2H)-pyrimidine dicarboxylic acid bis (ethyl ester);

3,6-dihydro-4-methyl-6-(2-ethoxy-6-pentadecylphenyl)-2-thioxo-1,5(2H)-pyrimidine dicarboxylic acid bis (ethyl ester);

3,6-dihydro-4-methyl-6-(2-isopropoxy-6-pentadecylphenyl)-2-thioxo-1,5(2H)-pyrimidine dicarboxylic acid bis (ethyl ester);

3,6-dihydro-4-methyl-6-(2-methoxy-6-dodecylphenyl)-2-thioxo-1,5(2H)-pyrimidine dicarboxylic acid bis(ethyl ester);

3,6-dihydro-4-methyl-6-(2-ethoxy-6-dodecylphenyl)-2-thioxo-1,5(2H)-pyrimidine dicarboxylic acid bis(ethyl ester);

3,6-dihydro-4-methyl-6-(2-isopropoxy-6-dodecylphenyl)-2-thioxo-1,5(2H)-pyrimidine dicarboxylic acid bis (ethyl ester);

3,6-dihydro-4-methyl-2-thioxo-6-[2-isopropoxy-6-pentadecylphenyl]-1,5(2H)-pyrimidine dicarboxylic acid 5-ethyl1-[1-(phenylmethyl)-4-piperidinyl]ester mono hydrochloride;

3,6-dihydro-4-methyl-2-thioxo-6-[2-ethoxy-6-pentadecylphenyl]-1,5(2H)-pyrimidine dicarboxylic acid 5-ethyl2-[1-(phenylmethyl)-4-piperidinyl]ester mono hydrochloride;

1,2,3,4-tetrahydro-6-methyl-4-[2-methoxy-6-pentadecylphenyl]-3-(1-oxo-propyl)-2-thioxo-5-pyrimidine carboxylic acid ethyl ester;

1,2,3,4-tetrahydro-6-methyl-4-[2-ethoxy-6-pentadecylphenyl]-3-(1-oxo-propyl)-2-thioxo-5-pyrimidine carboxylic acid ethyl ester;

1,2,3,4-tetrahydro-6-methyl-4-[2-isopropoxy-6-pentadecylphenyl]-3-(1-oxo-propyl)-2-thioxo-5-pyrimidine carboxylic acid ethyl ester;

1-[(dimethyl amino)carbonyl]-1,2,3,6-tetrahydro-4-methyl-6-[2-methoxy-6-pentadecylphenyl]-2-thioxo-5-pyrimidine carboxylic acid ethyl ester;

1-[(dimethyl amino)carbonyl]-1,2,3,6-tetrahydro-4-methyl-6-[2-ethoxy-6-pentadecylphenyl]-2-thioxo-5-pyrimidine carboxylic acid ethyl ester;

1-[(dimethyl amino)carbonyl]-1,2,3,6-tetrahydro-4-methyl-6-[2-isopropoxy-6-pentadecylphenyl]-2-thioxo-5-pyrimidine carboxylic acid ethyl ester;

3,6-dihydro-4-methyl-2-thioxo-6-[2-methoxy-6-pentadecylphenyl)]-1,5(2H)-pyrimidinedicarboxylic acid, 5-ethyl-1-[1-(phenmethyl)-4-piperidinyl]ester, monohydrochloride;

3,6-dihydro-4-methyl-2-thioxo-6-[2-methoxy-6-pentadecylphenyl)]-1,5(2H)-pyrimidinedicarboxylic acid, 5-(1-methylethyl) 1-[1-(phenmethyl)-4-piperidinyl]ester, monohydrochloride;

3,6-dihydro-4-methyl-2-thioxo-6-[2-ethoxy-6-pentadecylphenyl]-1,5(2H)-pyrimidinedicarboxylic acid, 5-(1-methylethyl) 1-[1-(phenylmethyl)-4-piperidinyl]ester, monohydrochloride;

3,6-dihydro-4-methyl-2-thioxo-6-[2-ethoxy-3,5-dinitro-6-pentadecylphenyl]-1,5(2H)-pyrimidinedicarboxylic acid, 5-(1-methylethyl) 1-[1-(phenylmethyl)-4-piperidinyl]ester, monohydrochloride;

1,2,3,6-Tetrahydro-4-methyl-1-[3-[methyl(phenylmethyl) amino]propyl]-2-thioxo-6-[2-methoxy-6-pentadecylphenyl]-5-pyrimidinecarboxylic acid, 1-methylethyl ester, monohydrochloride;

1,2,3,6-Tetrahydro-4-methyl-1-[2-[1-(phenylmethyl)-4-piperidinyl]ethyl]-2-thioxo-6-[2-methoxy-6-pentadecylphenyl)-5-pyrimidinecarboxylic acid, 1-methylethyl ester, monohydrochloride;

3,6-dihydro-4-methyl-2-thioxo-6-[2-ethoxy-6-pentadecylphenyl]-1,5(2H)-pyrimidinedicarboxylic acid, 1-[1-[(4-florophenyl)methyl]-4-piperidinyl]5-(1-methylethyl) ester, monohydrochloride;

4-ethyl-5-methoxycarbonyl-1-{N-[3 [4-(4-methoxycarbonyl)-4-phenylpiperidin-1-yl]propyl]carboxamido}-6-[2-methoxy-6-pentadecylphenyl]-2-oxo-1,2,3,6-tetrahydropyrimidine;

4-ethyl-5-methoxycarbonyl-1-{N-[3 [4-(4-methoxycarbonyl)-4-phenylpiperidin-1-yl]propyl]carboxamido}-6-[2-ethoxy-6-pentadecylphenyl]-2-oxo-1,2,3,6-tetrahydropyrimidine;

5-carboxamido-4-ethyl-1-{N-[3-[4-(4-methoxycarbonylphenylpiperidin-1-yl]-propyl]carboxamido}-6-[2-methoxy-6-pentadecylphenyl]-2-oxo-1,2,3,6-tetrahydropyrimidine;

4-ethyl-5-(N-methylcarboxamido)-1-{N-[3-(4-methoxycarbonylphenylpiperidin-1-yl)propyl]carboxamido}-6-[2-methoxy-6-pentadecylphenyl]-2-oxo-1,2,3,6-tetrahydropyrimidine;

5-methoxycarbonyl-1-{N-[3-[4-(4-methoxycarbonyl)-4-phenylpiperidin-1-yl]propyl]carboxamido}-4-methyl-6-[2-methoxy-6-pentadecylphenyl]-2-oxo-1,2,3,6-tetrahydropyrimidine;

5-ethoxycarbonyl-1-{N-[3-[4-(4-methoxycarbonyl)-4-phenylpiperidin-1-yl]propyl]carboxamido}-4-methyl-6-[2-methoxy-6-pentadecylphenyl]-2-oxo-1,2,3,6-tetrahydropyrimidine;

5-carboxamido-1-{N-[3-[4-(4-methoxycarbonyl)-4-phenylpiperidin-1-yl]propyl]carboxamido}-4-methyl-6-[2-methoxy-6-pentadecylphenyl]-2-oxo-1,2,3,6-tetrahydropyrimidine; and 1-{N-[3-[4-(4-methoxycarbonyl)-4-phenylpiperidin-1-yl]propyl]carboxamido}-4-methyl-5-(N-methylcarboxamido)-6-[2-methoxy-6-pentadecylphenyl]-2-oxo-1,2,3,6-tetrahydropyrimidine.

25. A method of treating hypertension comprising:

a) identifying a subject in need of such treatment;

b) administering to said subject a therapeutically effective amount of a compound of claim 1.

26. The method of claim 25, wherein said subject is a human.

27. A pharmaceutical composition comprising a compound of claim 1, and a physiologically acceptable carrier, diluent, or excipient, or a combination thereof.

* * * * *